(12) United States Patent
Lee et al.

(10) Patent No.: US 11,337,642 B2
(45) Date of Patent: May 24, 2022

(54) METHOD FOR PROVIDING INFORMATION RELATED TO SKIN AND ELECTRONIC DEVICE USING THE SAME

(71) Applicant: Samsung Electronics Co., Ltd., Gyeonggi-do (KR)

(72) Inventors: Jaesung Lee, Gyeonggi-do (KR); Jinhee Won, Gyeonggi-do (KR); Daehyeong Lim, Gyeonggi-do (KR); Dongwook Kim, Seoul (KR); Jongmin Choi, Seoul (KR); Minho Park, Gyeonggi-do (KR); Intaek Oh, Gyeonggi-do (KR); Donghyun Lee, Gyeonggi-do (KR); Taeho Kim, Chungcheongbuk-do (KR); Seungeun Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 472 days.

(21) Appl. No.: 15/927,154

(22) Filed: Mar. 21, 2018

(65) Prior Publication Data
US 2018/0271431 A1    Sep. 27, 2018

(30) Foreign Application Priority Data

Mar. 21, 2017    (KR) .................. 10-2017-0035569

(51) Int. Cl.
*A61B 5/00* (2006.01)
*A61B 5/024* (2006.01)
(Continued)

(52) U.S. Cl.
CPC .......... *A61B 5/443* (2013.01); *A61B 5/02416* (2013.01); *A61B 5/1032* (2013.01);
(Continued)

(58) Field of Classification Search
CPC ..... A61B 5/443; A61B 5/444; A61B 5/02416; A61B 5/6844; A61B 5/1032; A61B 5/445;
(Continued)

(56) References Cited

U.S. PATENT DOCUMENTS

| | | | |
|---|---|---|---|
| 10,531,820 B2* | 1/2020 | De Haan | A61B 5/6887 |
| 2003/0135098 A1* | 7/2003 | Lockhart | A61B 5/411 |
| | | | 600/310 |

(Continued)

FOREIGN PATENT DOCUMENTS

| | | |
|---|---|---|
| KR | 10-2016-0100770 A | 8/2016 |
| KR | 10-2016-0121307 A | 10/2016 |

(Continued)

OTHER PUBLICATIONS

European Search Report dated Aug. 21, 2018.
Korean Search Report dated May 21, 2021.
Chinese Search Report dated Nov. 29, 2021.

*Primary Examiner* — Jacqueline Cheng
*Assistant Examiner* — Tho Q Tran
(74) *Attorney, Agent, or Firm* — Cha & Reiter, LLC

(57) ABSTRACT

An electronic device and method are disclosed herein. The electronic device includes a sensor and a processor. The processor implements the method, including measuring infrared light corresponding to a user using the sensor, and detecting biometric information of the user if the infrared information satisfies a predetermined condition.

18 Claims, 25 Drawing Sheets

(51) Int. Cl.
   *A61B 5/103* (2006.01)
   *G06K 9/62* (2022.01)
   *G06T 7/00* (2017.01)

(52) U.S. Cl.
   CPC .............. *A61B 5/442* (2013.01); *A61B 5/444* (2013.01); *A61B 5/445* (2013.01); *A61B 5/6844* (2013.01); *A61B 5/6898* (2013.01); *A61B 5/743* (2013.01); *G06K 9/6215* (2013.01); *G06T 7/0012* (2013.01); *A61B 2560/0233* (2013.01); *A61B 2560/0462* (2013.01); *A61B 2562/043* (2013.01); *G06T 2207/30076* (2013.01)

(58) Field of Classification Search
   CPC ....... A61B 5/442; A61B 5/743; A61B 5/6898; A61B 2560/0233; A61B 2562/043; A61B 2560/0462; A61B 5/0059; A61B 2562/06; G06K 9/6215; G06T 7/0012; G06T 2207/30076
   See application file for complete search history.

(56) References Cited

U.S. PATENT DOCUMENTS

| | | | |
|---|---|---|---|
| 2009/0182208 A1* | 7/2009 | Cho | A61B 5/1032 600/310 |
| 2010/0198026 A1* | 8/2010 | Young | A61B 5/1032 600/306 |
| 2012/0120384 A1* | 5/2012 | Barrett | A61B 5/1455 356/41 |
| 2013/0129209 A1 | 5/2013 | Reid et al. | |
| 2013/0217984 A1* | 8/2013 | Graaff | A61B 5/7278 600/316 |
| 2013/0317367 A1 | 11/2013 | Shuler | |
| 2014/0180042 A1* | 6/2014 | Addison | A61B 5/7221 600/324 |
| 2014/0275852 A1 | 9/2014 | Hong et al. | |
| 2015/0230863 A1* | 8/2015 | Youngquist | A61B 5/4833 606/9 |
| 2015/0236740 A1 | 8/2015 | De Haan | |
| 2016/0125228 A1 | 5/2016 | Son et al. | |
| 2016/0199002 A1* | 7/2016 | Lee | A61B 5/6844 340/870.07 |
| 2016/0278646 A1* | 9/2016 | Hu | A61B 5/7475 |
| 2016/0235341 A1 | 10/2016 | Hwang et al. | |
| 2016/0287110 A1 | 10/2016 | Morris et al. | |
| 2016/0296119 A1 | 10/2016 | Nakamura et al. | |
| 2016/0296172 A1 | 10/2016 | Shi et al. | |
| 2016/0300471 A1* | 10/2016 | Hwang | G08B 21/24 |
| 2017/0042485 A1 | 2/2017 | Chung et al. | |

FOREIGN PATENT DOCUMENTS

| | | |
|---|---|---|
| KR | 10-2017-0019745 A | 2/2017 |
| WO | 2013/070864 A2 | 5/2013 |
| WO | 2013/077808 A1 | 5/2013 |

\* cited by examiner

FIG. 13
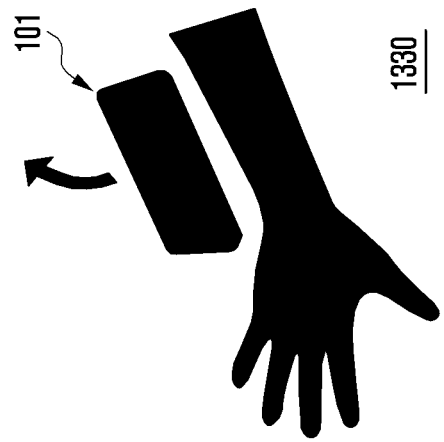
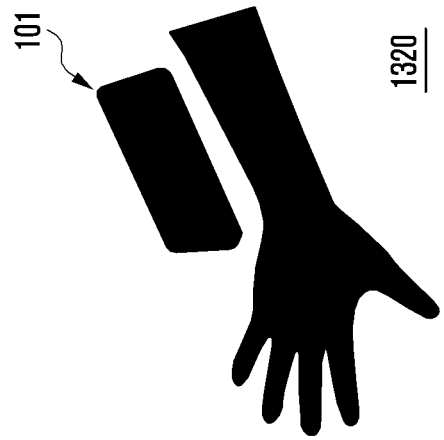
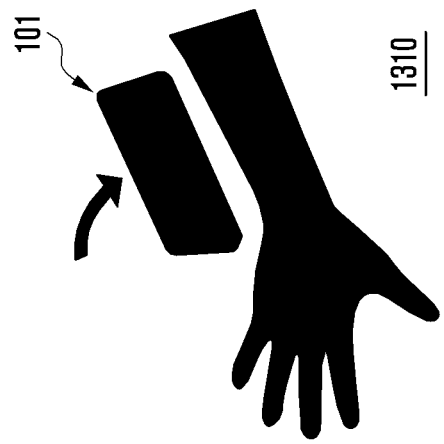

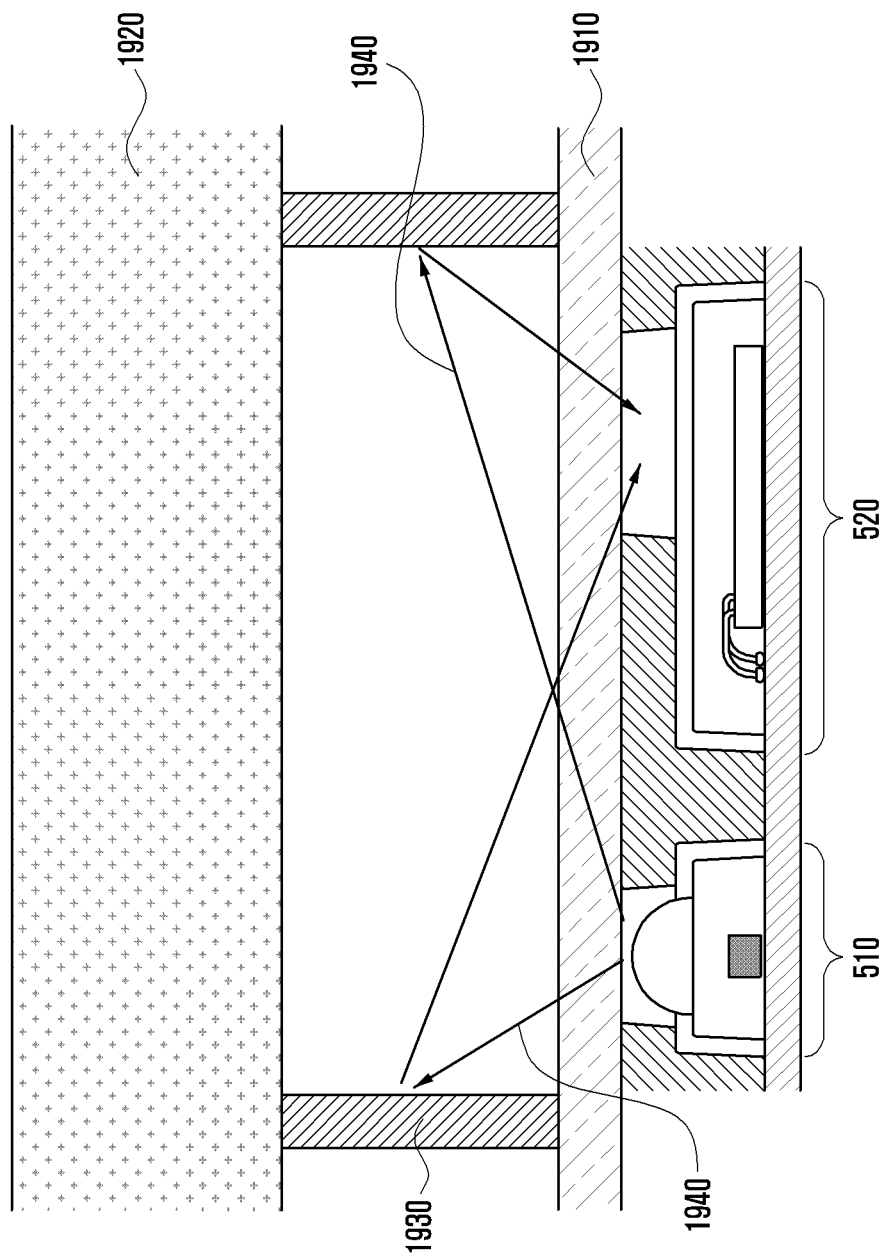

METHOD FOR PROVIDING INFORMATION RELATED TO SKIN AND ELECTRONIC DEVICE USING THE SAME

CLAIM OF PRIORITY

This application claims priority from and the benefit under 35 U.S.C. § 119(a) of Korean Patent Application No. 10-2017-0035569 filed on Mar. 21, 2017, which is hereby incorporated by reference for all purposes as if fully set forth herein.

TECHNICAL FIELD

The present disclosure relates to a method for providing information related to skin and an electronic device using the same.

BACKGROUND

These days, information related to a user's skin can be measured through an optical skin measuring sensor. In case of a general optical skin measuring sensor, products for research, products for medicine, and products for beauty are equipped with a plurality of optical components and can be designed to have an optical path of a specific distance in order to separate wavelength information. For example, indexes related to the user's skin (e.g., melanin index, erythema index, and skin tone) can be provided based on the wavelength information.

SUMMARY

Generally, an optical skin measuring sensor may have difficulties in miniaturization because of structural problems in satisfying conditions of securing an optical path and blocking an external light. Accordingly, difficulties may be encountered when installing the optical skin measuring sensor in an electronic device such as a portable terminal. For example, in order to install the skin measuring sensor at the front or rear side of the portable terminal, a separate hole may be formed additionally or any sensor installed in an existing hole may be replaced with the skin measuring sensor. In relation to this, a method of forming a separate hole may give an influence to an aesthetic appearance. Further, in case of replacing an existing sensor with a skin measuring sensor, problems may occur because the functions of the existing sensor (e.g., heartrate measurement and proximity recognition) cannot be used.

Separately from the problem of installing the skin measuring sensor, other problems may occur in a method for performing a skin measurement. For example, it may be inconvenient to touch a skin measuring sensor to a user's skin or maintain a specific distance between the skin measuring sensor and the user's skin under the condition of blocking an external light.

An electronic device according to various embodiments of the present disclosure can provide information related to skin as well as functions provided by a pre-installed sensor (e.g., heart rate monitor (HRM) sensor or photoplethysmogram (PPG) sensor) by modifying the structure of the pre-installed sensor. For example, the electronic device can provide information of a melanin index, erythema index, and skin tone based on information of visible light (e.g., red and green light) and an infrared (IR) light. In particular, by using a pre-installed sensor, a design change of an electronic device by adding a skin measuring sensor or forming a hole may be unnecessary.

An electronic device is disclosed, including a sensor, and a processor. The processor is configured to measure infrared light corresponding to a user using the sensor, and detect biometric information of the user if the measured infrared light satisfies a predetermined condition.

A method in an electronic device is disclosed, including measuring infrared light corresponding to a user using a sensor, and detecting the biometric information of a user if the measured infrared light satisfies a predetermined condition.

BRIEF DESCRIPTION OF THE DRAWINGS

The above and other aspects and features of certain embodiments of the present disclosure will be more apparent from the following description taken in conjunction with the accompanying drawings, in which:

FIG. 13 illustrates a method for performing a non-contact measurement in an electronic device according to various embodiments of the present disclosure;

FIG. 19A, FIG. 19B and FIG. 19C are cross sectional views illustrating a method for measuring information related to skin by attaching an external accessory to an electronic device according to various embodiments of the present disclosure.

DETAILED DESCRIPTION

Figure 1:
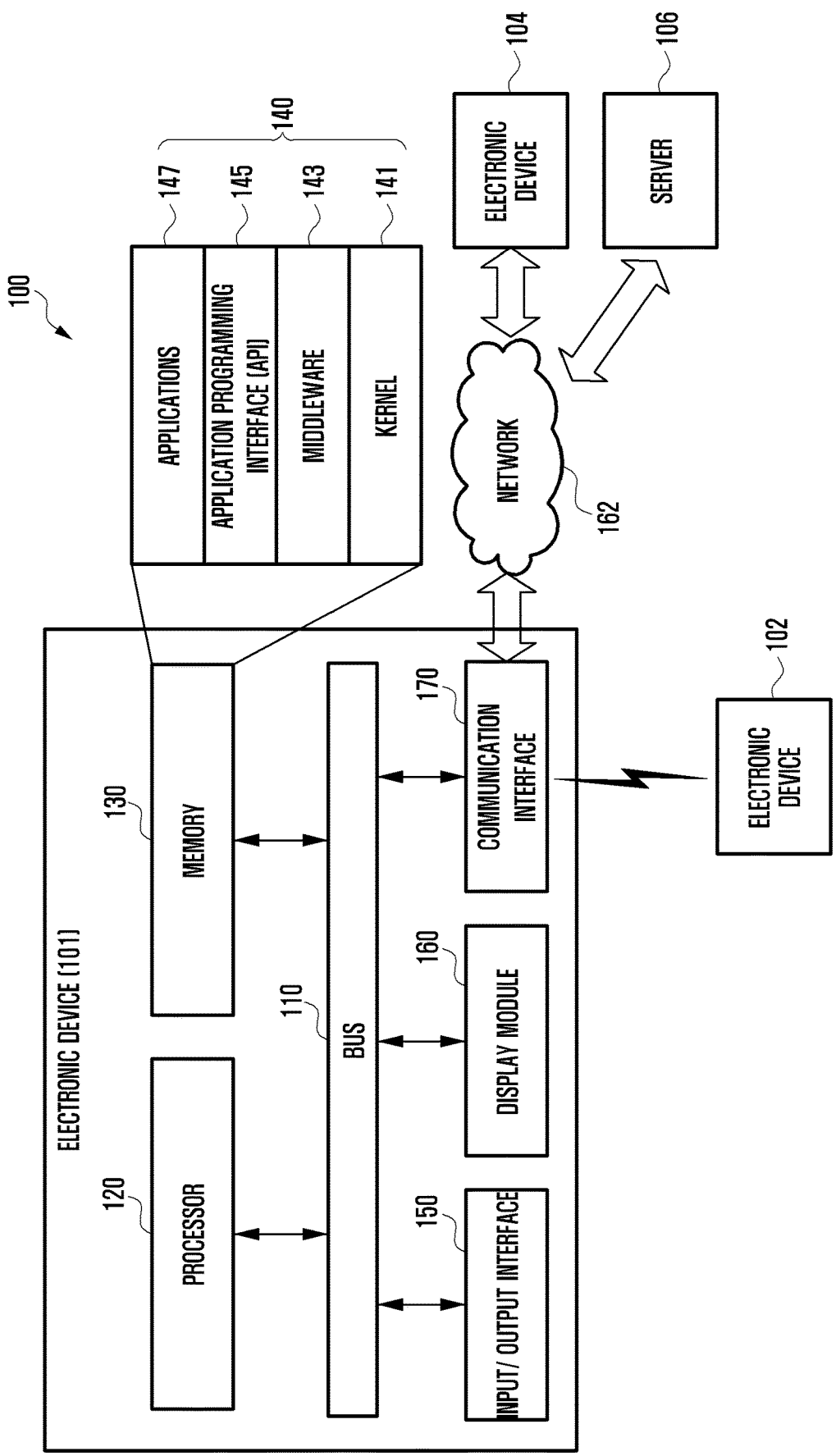
FIG. 1 is a block diagram illustrating a network environment including an electronic device according to various embodiments of the present disclosure.

Hereinafter, embodiments of the present disclosure are described in detail with reference to the accompanying drawings. While the present disclosure may be embodied in many different forms, specific embodiments of the present disclosure are shown in drawings and are described herein in detail, with the understanding that the present disclosure is to be considered to be limited thereto. The same reference numerals are used throughout the drawings to refer to the same or like parts.

An expression "comprising" or "may comprise" used in the present disclosure indicates presence of a corresponding function, operation, or element and does not limit an additional at least one function, operation, or element. The term "comprise" or "have" used herein indicates presence of a characteristic, numeral, step, operation, element, component, or combination thereof described in the Specification and does not exclude presence or addition of at least one other characteristic, numeral, step, operation, element, component, or combination thereof.

In the present disclosure, the term "or" includes any combination or the entire combination of together listed words. For example, "A or B" may include A, B, or A and B.

Expressions such as "a first" and "a second" in the present disclosure may represent various elements of the present disclosure, but do not limit corresponding elements, e.g., do not limit order and/or importance of corresponding elements, but may be used for distinguishing one element from another element. For example, both a first user device and a second user device are user devices and represent different user devices. For example, a first constituent element may be referred to as a second constituent element without deviating from the present disclosure, and similarly, a second constituent element may be referred to as a first constituent element.

When it is described that a first element is "coupled" to another element, such as a second element, the first element may be "directly coupled" to the second element or "electrically coupled" to the second element through a third element. However, when it is described that a first element is "directly coupled" to a second element, no third element may exist between the first and second elements.

Terms used in the present disclosure are not intended to limit the present disclosure but to illustrate embodiments of the present disclosure. When using in a description of the present disclosure and the appended claims, a singular form includes a plurality of forms unless it is explicitly differently represented.

Unless differently defined, terms including a technical term and a scientific term used herein have the same meaning as may be generally understood by a person of common skill in the art. It should be understood that generally using terms defined in a dictionary have a meaning corresponding to that of a context of related technology and are not understood to have an ideal or excessively formal meaning unless explicitly defined.

In this disclosure, an electronic device may have a communication function. For example, an electronic device may be a smart phone, a tablet PC, a mobile phone, a video phone, an e-book reader, a desktop PC, a laptop PC, a netbook computer, a PDA (personal digital assistant), a PMP (portable multimedia player), an MP3 player, a portable medical device, a digital camera, or a wearable device, such as an HMD (head-mounted device) in the form of electronic glasses, electronic clothes, an electronic bracelet, an electronic necklace, an electronic appcessory, or a smart watch.

According to some embodiments, an electronic device may be a smart home appliance that involves a communication function, such as a TV (television), a DVD (digital video disk) player, audio equipment, a refrigerator, an air conditioner, a vacuum cleaner, an oven, a microwave, a washing machine, an air cleaner, a set-top box, a TV box, such as Samsung HomeSync™, Apple TV™, and Google TV™, a game console, an electronic dictionary, an electronic key, a camcorder, or an electronic picture frame.

According to some embodiments, an electronic device may be a medical device, such as MRA (magnetic resonance angiography), MRI (magnetic resonance imaging), CT (computed tomography), and ultrasonography, a navigation device, a GPS (global positioning system) receiver, an EDR (event data recorder), an FDR (flight data recorder), a car infotainment device, electronic equipment for ship, such as a marine navigation system or a gyrocompass), avionics, security equipment, or an industrial or home robot.

According to some embodiments, an electronic device may be furniture or part of a building or construction having a communication function, an electronic board, an electronic signature receiving device, a projector, or various measuring instruments, such as a water, electric, gas, or a wave meter. An electronic device disclosed herein may be one of the above-mentioned devices or any combination thereof. As well understood by those skilled in the art, the above-mentioned electronic devices are not to be considered as a limitation of the present disclosure.

According to embodiments, the electronic device may control the activation of a second sensor, based on a signal received through a first sensor, which reduces power consumption of the electronic device compared to a conventional device, in which the second sensor is continuously activated. The electronic device according to embodiments of the present disclosure may perform a predefined function in response to the signal received through the second sensor.

FIG. 1 is a block diagram illustrating an electronic apparatus 100 including an electronic device 101 according to an embodiment of the present disclosure.

Referring to FIG. 1, the electronic device 101 may include a bus 110, a processor 120, a memory 130, a user input module (i.e., input/output interface) 150, a display 160, and a communication interface 170.

The bus 110 may be a circuit for interconnecting elements of the electronic device 101 and for allowing a communication, such as by transferring a control message, between the elements.

The processor 120 can receive commands from the memory 130, the user input module 150, the display 160, and the communication interface 170, through the bus 110, can decipher the received commands, and perform operations and/or data processing according to the deciphered commands.

The memory 130 can store commands received from the processor 120 and/or other elements, and/or commands and/or data generated by the processor 120 and/or other elements.

The memory 130 may include software and/or programs 140, such as a kernel 141, middleware 143, an application programming interface (API) 145, and an application 147. Each of the programming modules described above may be configured by software, firmware, hardware, and/or combinations of at least two thereof.

The kernel 141 can control and/or manage system resources used for execution of operations and/or functions implemented in other programming modules, such as the middleware 143, the API 145, and/or the applications 147, and can provide an interface through which the middleware 143, the API 145, and/or the applications 147 can access and then control and/or manage an individual element of the electronic apparatus 100.

The middleware 143 can perform a relay function which allows the API 145 and/or the applications 147 to communicate with and exchange data with the kernel 141. In relation to operation requests received from at least one of applications 147, the middleware 143 can perform load balancing in relation to the operation requests by giving a priority in using a system resource, e.g. the bus 110, the processor 120, and/or the memory 130, of the electronic apparatus 100 to at least one application from among the at least one of the applications 147.

The API 145 is an interface through which the applications 147 can control a function provided by the kernel 141 and/or the middleware 143, and may include at least one interface or function for file control, window control, image processing, and/or character control.

The user input module 150 can receive a command and/or data from a user, and transfer the received command and/or data to the processor 120 and/or the memory 130 through the bus 110. The display 160 can display an image, a video, and/or data to a user.

The communication interface 170 can establish a communication between the electronic apparatus 100 and another electronic devices 102 and 104 and/or a server 106, and can support short range communication protocols, e.g. a wireless fidelity (WiFi) protocol, a BlueTooth (BT) protocol, and a near field communication (NFC) protocol, communication networks, e.g. Internet, local area network (LAN), wide area network (WAN), a telecommunication network, a cellular network, and a satellite network, a plain old telephone service (POTS), or any other similar and/or suitable communication networks, such as network 162. Each of the electronic devices 102 and 104 may be the same type or different types of electronic devices.

Figure 2:
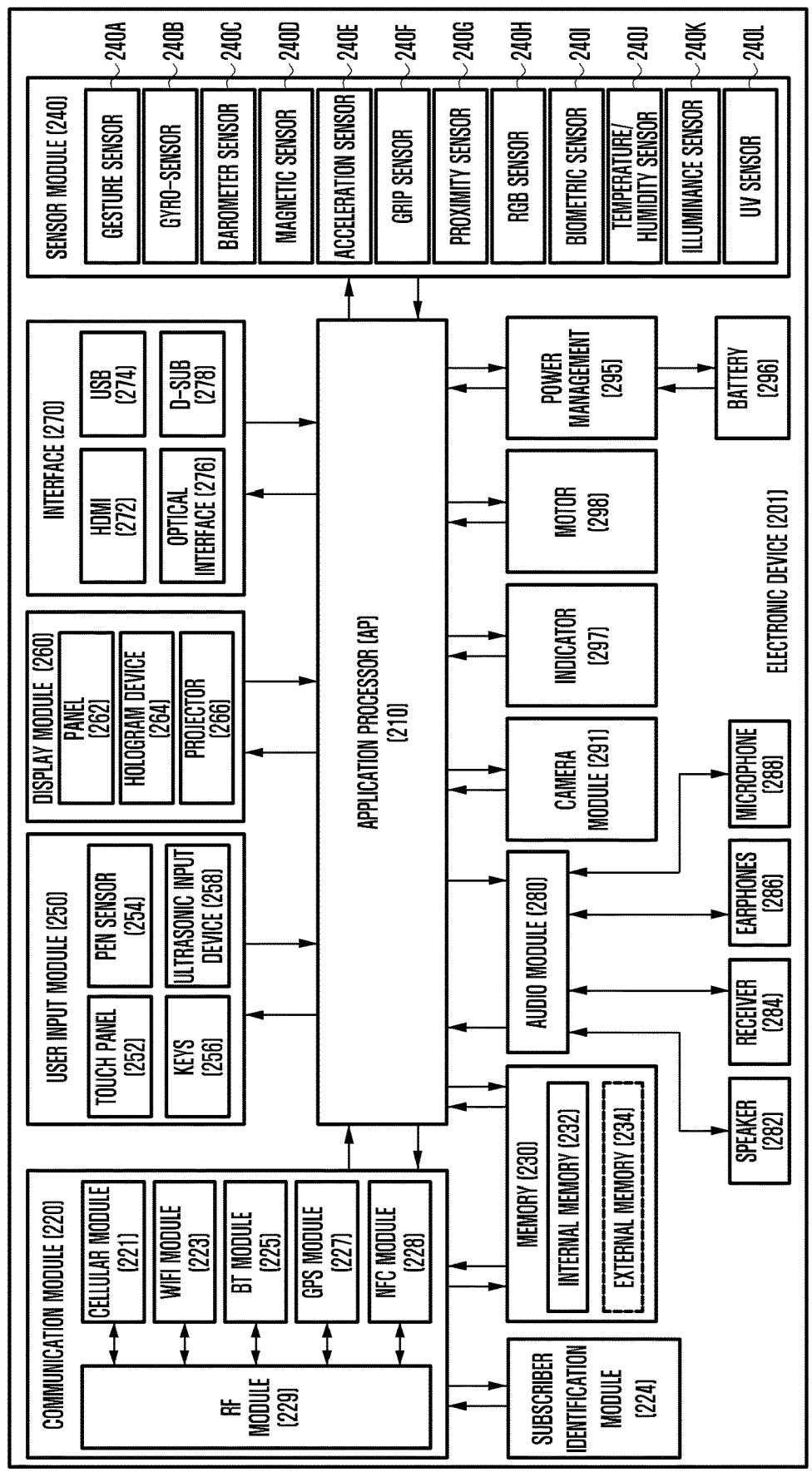
FIG. 2 is a block diagram illustrating a configuration of an electronic device according to various embodiments of the present disclosure.

FIG. 2 illustrates an electronic device 201 in accordance with an embodiment of the present disclosure. The electronic device 201 may form all or part of the electronic device 101 shown in FIG. 1.

Referring to FIG. 2, the electronic device 201 may include at least one application processor (AP) 210, a communication module 220, a subscriber identification module (SIM) card 224, a memory 230, a sensor module 240, an input unit 250, a display 260, an interface 270, an audio module 280, a camera module 291, a power management module 295, a battery 296, an indicator 297, and a motor 298.

The AP 210 may drive an operating system or applications, control a plurality of hardware or software components connected thereto, and also perform processing and operation for various data including multimedia data. The AP 210 may be formed of a system-on-chip (SoC), and may further include a graphic processing unit (GPU).

The communication module 220 may perform a data communication with any other electronic device connected to the electronic device 201 through the network. According to an embodiment, the communication module 220 may include therein a cellular module 221, a WiFi module 223, a BT module 225, a GPS module 227, an NFC module 228, and an RF (radio frequency) module 229.

The cellular module 221 may offer a voice call, a video call, a message service, or an Internet service through a communication network, such as long term evolution (LTE), LTE-advanced (LTE-A), code division multiple access (CDMA), wideband CDMA (WCDMA), universal mobile telecommunications system (UMTS), WiBro, or global system for mobile communication (GSM). Additionally, the cellular module 221 may perform identification and authentication of the electronic device in the communication network, using the SIM card 224. According to an embodiment, the cellular module 221 may perform at least part of functions the AP 210 can provide, such as a multimedia control function.

According to an embodiment, the cellular module 221 may include a communication processor (CP), and may be formed of an SoC, for example. Although some elements such as the cellular module 221, such as the CP, the memory 230, or the power management module 295 are shown as separate elements being different from the AP 210 in FIG. 2, the AP 210 may be formed to have at least part of the above elements in an embodiment of the present disclosure.

According to an embodiment, the AP 210 or the cellular module 221 may load commands or data, received from a nonvolatile memory connected thereto or from at least one of the other elements, into a volatile memory to process them. Additionally, the AP 210 or the cellular module 221 may store data, received from or created at one or more of the other elements, in the nonvolatile memory.

Each of the WiFi module 223, the BT module 225, the GPS module 227 and the NFC module 228 may include a processor for processing data transmitted or received therethrough. Although FIG. 2 illustrates the cellular module 221, the WiFi module 223, the BT module 225, the GPS module 227 and the NFC module 228 as different blocks, at least two of these modules may be contained in a single IC (integrated circuit) chip or a single IC package, i.e., may be formed as a single SoC.

The RF module 229 may transmit and receive RF signals or any other electric signals, and may include a transceiver, a PAM (power amp module), a frequency filter, or an LNA (low noise amplifier). The RF module 229 may further include any component, e.g., a wire or a conductor, for transmission of electromagnetic waves in a free air space. Although FIG. 2 illustrates that the cellular module 221, the WiFi module 223, the BT module 225, the GPS module 227 and the NFC module 228 share the RF module 229, at least one of these modules may perform transmission and reception of RF signals through a separate RF module in an embodiment of the present disclosure.

The SIM card 224 may be a specific card formed of SIM and may be inserted into a slot formed at a certain location of the electronic device. The SIM card 224 may contain therein an ICCID (integrated circuit card identifier) or an IMSI (international mobile subscriber identity).

The memory 230 may include an internal memory 232 and an external memory 234. The internal memory 232 may include at least one of a volatile memory, such as DRAM (dynamic random access memory), SRAM (static RAM), SDRAM (synchronous DRAM), or a nonvolatile memory, such as OTPROM (one time programmable read-only memory), PROM (programmable ROM), EPROM (erasable and programmable ROM), EEPROM (electrically erasable and programmable ROM), mask ROM, flash ROM, NAND flash memory, and NOR flash memory.

According to an embodiment, the internal memory 232 may have the form of an SSD (solid state drive). The external memory 234 may include a flash drive, e.g., CF (compact flash), SD (secure digital), Micro-SD (micro secure digital), Mini-SD (mini secure digital), xD (extreme digital), or memory stick, and may be functionally connected to the electronic device 201 through various interfaces. The electronic device 201 may further include a storage device or medium such as a hard drive.

The sensor module 240 may measure physical quantity or sense an operating status of the electronic device 201, and then convert measured or sensed information into electric signals. The sensor module 240 may include at least one of a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H, such as an RGB (red, green, blue) sensor, a biometric sensor 240I, a temperature-humidity sensor 240J, an illumination sensor 240K, and a UV (ultraviolet) sensor 240L. Additionally or alternatively, the sensor module 240 may include an E-nose sensor, an EMG (electromyography) sensor, an EEG (electroencephalogram) sensor, an ECG (electrocardiogram) sensor, an IR (infrared) sensor, an iris scan sensor, or a finger scan sensor. The sensor module 240 may include a control circuit for controlling one or more sensors equipped therein.

The input unit 250 may include a touch panel 252, a digital pen sensor 254, a key 256, or an ultrasonic input device 258. The touch panel 252 may recognize a touch input in a capacitive, resistive, infrared, or ultrasonic type manner. The touch panel 252 may further include a control circuit. In case of a capacitive type, a physical contact or proximity may be recognized. The touch panel 252 may further include a tactile layer that offers a tactile feedback to a user.

The digital pen sensor 254 may be formed in the same or similar manner as receiving a touch input or by using a separate recognition sheet. The key 256 may include a physical button, an optical key, or a keypad. The ultrasonic input device 258 is capable of identifying data by sensing sound waves with a microphone (MIC) 288 in the electronic device 201 through an input tool that generates ultrasonic signals, thus allowing wireless recognition. According to an embodiment, the electronic device 201 may receive a user input from any external device connected thereto through the communication module 220.

The display 260 may include a panel 262, a hologram device 264, or a projector 266. The panel 262 may be LCD (liquid crystal display), or AM-OLED (active matrix organic light emitting diode) may have a flexible, transparent or wearable form, and may be formed of a single module with the touch panel 252. The hologram device 264 may project a stereoscopic image in the air using interference of light. The projector 266 may project an image onto a screen, which may be located at the inside or outside of the electronic device 201. According to an embodiment, the display 260 may further include a control circuit for controlling the panel 262, the hologram device 264, and the projector 266.

The interface 270 may include an HDMI (high-definition multimedia interface) 272, a USB (universal serial bus) 274, an optical interface 276, and a D-sub (d-subminiature) 278, and may be contained in the communication interface 170 shown in FIG. 1. Additionally or alternatively, the interface 270 may include an MHL (mobile high-definition link) interface, an SD (secure digital) card/MMC (multi-media card) interface, or an IrDA (infrared data association) interface.

The audio module 280 may perform a conversion between sounds and electric signals. At least part of the audio module 280 may be contained in the input/output interface 150 shown in FIG. 1. The audio module 280 may process sound information inputted or outputted through a speaker 282, a receiver 284, an earphone 286, or the MIC 288.

The camera module 291 is capable of obtaining still images and moving images, and may include at least one image sensor, such as a front sensor or a rear sensor, a lens, an ISP (image signal processor, or a flash, such as LED or xenon lamp.

The power management module 295 may manage electric power of the electronic device 201 and may include a PMIC (power management integrated circuit), a charger IC, or a battery gauge.

The PMIC may be formed of an IC chip or SoC. Charging may be performed in a wired or wireless manner. The charger IC may charge a battery 296 and prevent overvoltage or overcurrent from a charger. According to an embodiment, the charger IC may have a charger IC used for at least one of wired and wireless charging types. A wireless charging type may include a magnetic resonance type, a magnetic induction type, or an electromagnetic type. Any additional circuit for a wireless charging may be further used, such as a coil loop, a resonance circuit, or a rectifier.

The battery gauge may measure the residual amount of the battery 296 and a voltage, current or temperature in a charging process. The battery 296 may store or create electric power therein and supply electric power to the electronic device 201. The battery 296 may be a rechargeable or solar battery.

The indicator 297 may illustrate thereon a current status, such as a booting, message, or recharging status of part or all of the electronic device 201. The motor 298 may convert an electric signal into a mechanical vibration. The electronic device 201 may include a specific processor, such as GPU, for supporting a mobile TV. This processor may process media data that comply with standards of DMB (digital multimedia broadcasting), DVB (digital video broadcasting), or media flow.

Each of the above-discussed elements of the electronic device disclosed herein may be formed of one or more components, and may have various names according to the type of the electronic device. The electronic device disclosed herein may be formed of at least one of the above-discussed elements without some elements or with additional elements. Some of the elements may be integrated into a single entity that still performs the same functions as those of such elements before integrated.

Figure 3:
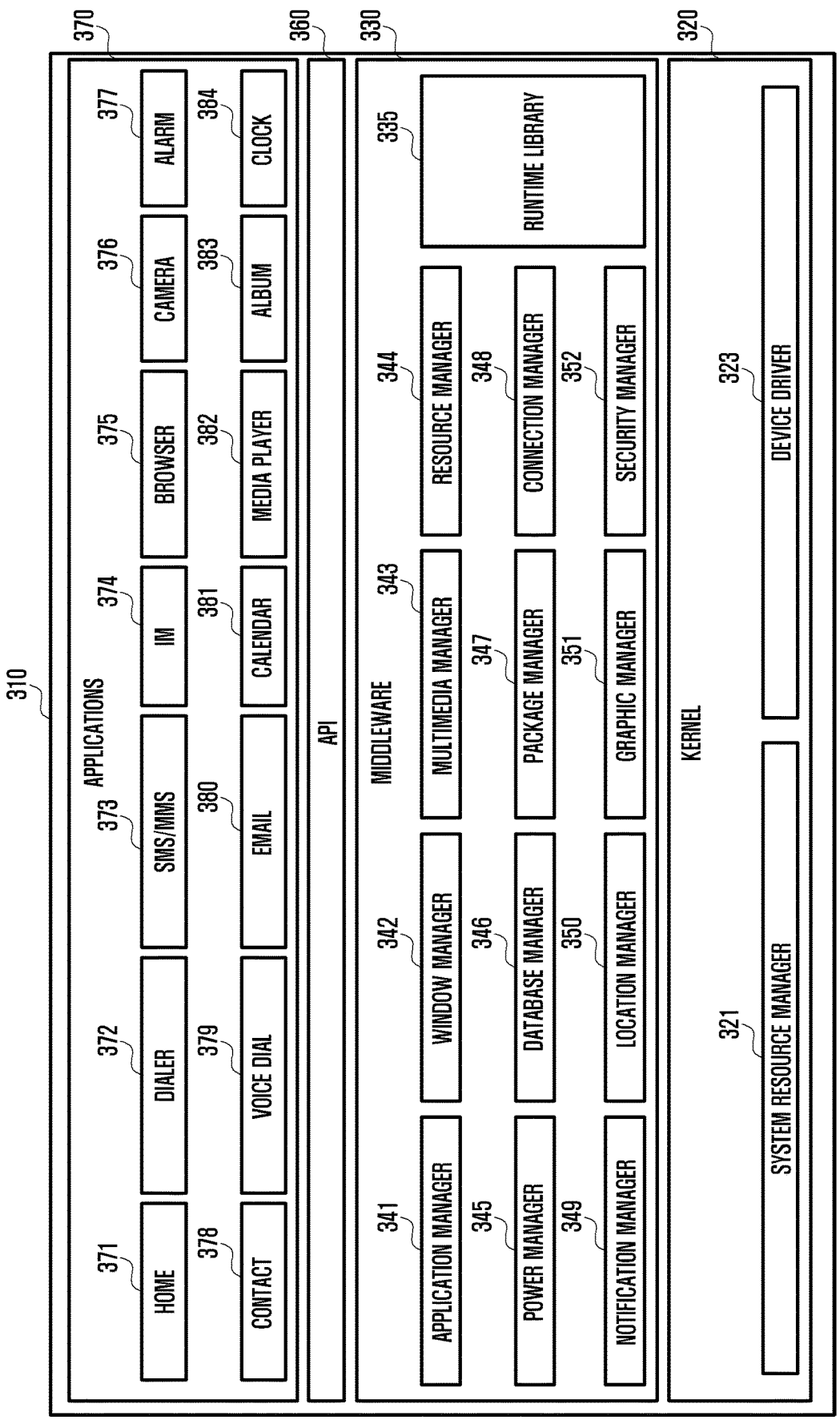
FIG. 3 is a block diagram illustrating a configuration of a program module according to various embodiments of the present disclosure.

FIG. 3 illustrates a configuration of a programming module 310 according to an embodiment of the present disclosure.

The programming module 310 may be stored in the electronic device 100 or may be stored in the electronic device 201 illustrated in FIG. 2. At least a part of the programming module 310 may be implemented in software, firmware, hardware, or a combination of two or more thereof. The programming module 310 may be implemented in hardware 201, and may include an OS controlling resources related to an electronic device and/or various applications 370 executed in the OS. For example, the OS may be Android, iOS, Windows, Symbian, Tizen, or Bada.

Referring to FIG. 3, the programming module 310 may include a kernel 320, middleware 330, an API 360, and/or applications 370.

The kernel 320 may include a system resource manager 321 and/or a device driver 323. The system resource manager 321 may include a process manager, a memory manager, and a file system manager. The system resource manager 321 may perform the control, allocation, or recovery of system resources. The device driver 323 may include a display driver, a camera driver, a Bluetooth driver, a shared memory driver, a USB driver, a keypad driver, a Wi-Fi driver, and/or an audio driver, and may further include an inter-process communication (IPC) driver. The middleware 330 may include multiple modules previously implemented so as to provide a function used in common by the applications 370, and may provide a function to the applications 370 through the API 360 in order to enable the applications 370 to efficiently use limited system resources within the electronic device. For example, as illustrated in FIG. 3, the middleware 330 may include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, a security manager 352, and any other suitable and/or similar manager.

The runtime library 335 may include a library module used by a complier, in order to add a new function by using a programming language during the execution of the applications 370, and may perform functions which are related to input and output, the management of a memory, or an arithmetic function.

The application manager 341 may manage a life cycle of at least one of the applications 370. The window manager 342 may manage GUI resources used on the screen. The multimedia manager 343 may detect a format used to reproduce various media files and may encode or decode a media file through a codec appropriate for the relevant format. The resource manager 344 may manage resources, such as a source code, a memory, or a storage space, of at least one of the applications 370.

The power manager 345 may operate together with a basic input/output system (BIOS), may manage a battery or power, and may provide power information used for an operation. The database manager 346 may manage a database in such a manner as to enable the generation, search and/or change of the database to be used by at least one of the applications 370. The package manager 347 may manage the installation and/or update of an application distributed in the form of a package file.

The connectivity manager 348 may manage a wireless connectivity such as Wi-Fi and Bluetooth. The notification manager 349 may display or report, to the user, an event such as an arrival message, an appointment, or a proximity alarm, in such a manner as not to disturb the user. The location manager 350 may manage location information of the electronic device. The graphics manager 351 may manage graphic effects, which are to be provided to the user, and/or a user interface related to the graphic effects. The security manager 352 may provide various security functions used for system security and user authentication. According to an embodiment of the present disclosure, when the electronic device has a telephone function, the middleware 330 may further include a telephony manager for managing a voice and/or video telephony call function of the electronic device.

The middleware 330 may generate and use new middleware module through various functional combinations of the above-described internal element modules, may provide modules specialized according to types of OSs in order to provide differentiated functions, and may dynamically delete some of the existing elements, or may add new elements. Accordingly, the middleware 330 may omit some of the elements described in the embodiments of the present disclosure, may further include other elements, or may replace the some of the elements with elements, each of which performing a similar function and having a different name.

The API 360 is a set of API programming functions, and may be provided with a different configuration according to an OS. In the case of Android or iOS, for example, one API set may be provided to each platform. In the case of Tizen, two or more API sets may be provided to each platform.

The applications 370 may include a preloaded application and/or a third party application, and may include a home 371, dialer 372, a short message service (SMS)/multimedia messaging service (MMS) 373, instant message (IM) 374, browser 375, camera 376, alarm 377, contact 378, voice dial 379, electronic mail (e-mail) 380, calendar 381, media player 382, album 383, and clock application 384, and any other suitable and/or similar application.

At least a part of the programming module 310 may be implemented by instructions stored in a non-transitory computer-readable storage medium. When the instructions are executed by one or more processors, the one or more processors may perform functions corresponding to the instructions. The non-transitory computer-readable storage medium may be the memory 230. At least a part of the programming module 310 may be executed by the one or more processors 210, and may include a module, a program, a routine, a set of instructions, and/or a process for performing one or more functions.

Figure 4:
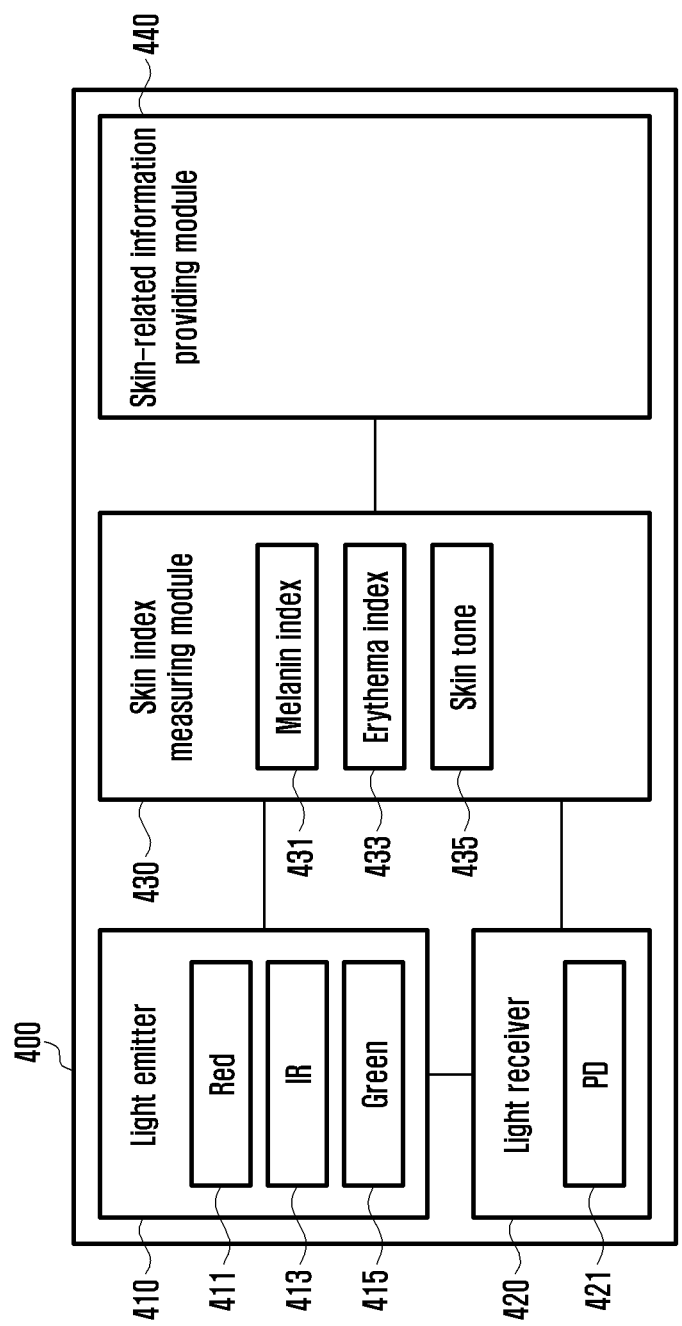
FIG. 4 is a schematic block diagram illustrating an information providing system related to skin according to various embodiments of the present disclosure.

FIG. 4 is a schematic block diagram illustrating an information providing system related to skin according to various embodiments of the present disclosure.

With reference to FIG. 4, a skin-related information providing system 400 may include a light emitter 410, light receiver 420, skin index measuring module 430, and skin-related information providing module 440. According to various embodiments, the skin index measuring module 430 can measure at least one index related to skin as a measurement target. For example, a melanin index 431, erythema index 433, and skin tone 435 can be measured as a measurement target of skin. Besides this, various skin indexes can be measured according to the type of light included in the light emitter 410. According to various embodiments, the skin-related information providing module 440 can provide information (e.g., at least one of beauty, clothes, health, and shopping) for a user based on the skin index measured by the skin index measuring module 430.

According to various embodiments, the electronic device 101 can measure and provide a user's skin-related information through the skin-related information providing system 400. For example, the electronic device 101 can measure at least one user's skin index such as a melanin index, erythema index, and skin tone, and can provide the measured skin index for the user.

According to various embodiments, the electronic device 101 can provide useful information for a user based on the skin index through the skin-related information providing system 400. For example, information related to ultraviolet exposure, burn hazard, recommended cosmetics, and recommended clothes can be provided. By recommending cosmetics and clothes, a user can be introduced to an online purchase, and use of online payment means (e.g., Samsung Pay) can be promoted.

According to various embodiments, the skin-related information providing system 400 can measure at least one skin index through the light emitter 410 and the light receiver 420.

According to various embodiments, the light emitter 410 can emit light in a band of visible light (at least one of red light 411, green light 415, and blue light (not shown)) and an infrared light (IR) 413. For reference, the light emitter 410 may include various color light sources besides the above light sources in order to obtain the skin-related information.

According to various embodiments, the light receiver 420 can absorb at least one part of light emitted by the light emitter 410 and reflected by a user's skin through at least one photodiode (PD) 421.

According to various embodiments, the skin-related information providing system 400 can emit light by combining different wavelengths according to the type of skin index to be measured, and it can measure at least one user's skin index by measuring an absorption rate or reflection rate of the emitted light. For example, the skin-related information providing system 400 can measure the melanin index 431 by emitting and absorbing light having 660/880 nm wavelength, erythema index 433 by emitting and absorbing light having 568/660 nm wavelength, and skin tone 435 by emitting and absorbing light having 568/660/880 nm wavelength. For example, among light sources of the light emitter 410, the red light 411 can emit a visible light having a 660 nm wavelength, the green light 415 can emit a visible light having a 568 nm wavelength, and the infrared light (IR) 413 can emit a light having an 880 nm wavelength.

Generally, an optical skin measuring sensor may have difficulties in miniaturization because of structural problems in satisfying conditions of securing an optical path and blocking an external light. Accordingly, difficulties may be encountered when installing the optical skin measuring sensor in an electronic device such as a portable terminal. For example, in order to install the skin measuring sensor at the front or rear side of the portable terminal, a separate hole can be formed additionally or any sensor installed in an existing hole can be replaced with the skin measuring sensor. In this connection, a method of forming a separate hole may give an influence to an aesthetic appearance. Further, in case of replacing the existing sensor with the skin measuring sensor, problems may occur because the functions of the existing sensor (e.g., heartrate measurement and proximity recognition) cannot be used.

According to various embodiments of the present disclosure, the electronic device 101 can provide information related to skin as well as functions provided by a pre-installed sensor (e.g., heart rate monitor (HRM) sensor or photoplethysmogram (PPG) sensor) by modifying the structure of the pre-installed sensor. In particular, by using a pre-installed sensor, a design change of an electronic device may be unnecessary for adding a skin measuring sensor or forming a hole.

According to various embodiments, the electronic device 101 can measure biometric information through a HRM sensor or a PPG sensor. For example, the HRM sensor or the PPG sensor can measure a heartrate, oxygen saturation, and stress index by using a visible light (e.g., red light having a 660 nm wavelength) and an infrared light having an 880 nm wavelength.

According to various embodiments, the electronic device 101 can additionally provide at least one skin index measurement function (e.g., measurement of a melanin index, erythema index, and skin tone) as well as functions of the existing HRM sensor or PPG sensor (e.g., measurement of a heartrate, oxygen saturation, and stress index) by adding a light source (e.g., light emitting diode; LED) emitting a green light with a 568 nm wavelength to a light emitter (e.g., light source emitting infrared and red lights). For example, the skin tone has a concept considering at least one of a hue, chroma, and brightness. However, skin tone distribution occurs in a partial area of the whole area including the hue, chroma, and brightness, and thereby the skin tone and erythema index can be measured by using red and green light in a visible light range and an infrared light (IR).

Figure 5:
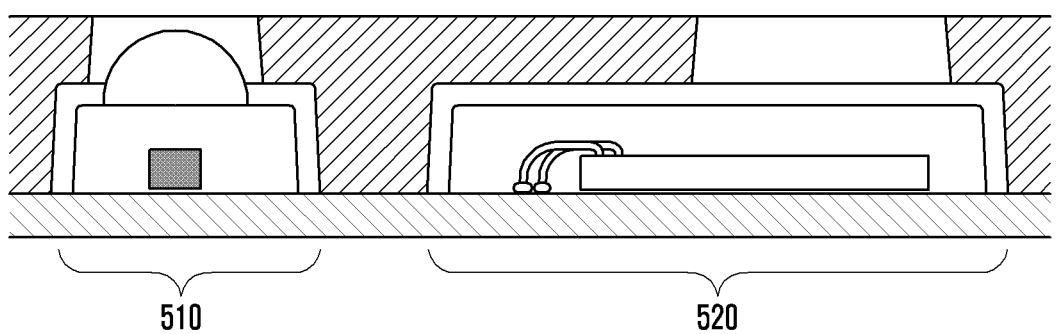
FIG. 5 is a cross sectional view illustrating structures of a light emitter and a light receiver of a sensor installed in an electronic device according to various embodiments of the present disclosure.
Figure 6:
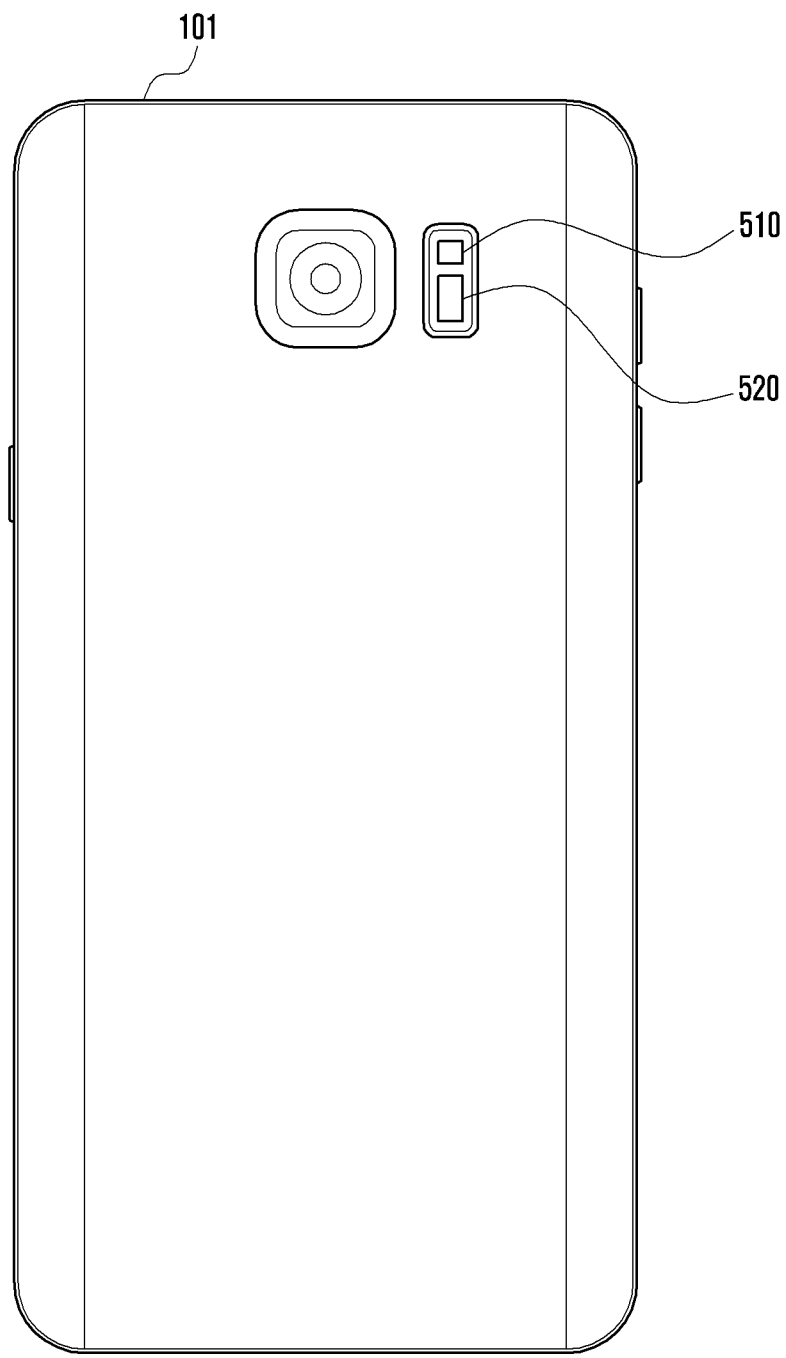
FIG. 6 is a rear view illustrating a sensor installed in an electronic device according to various embodiments of the present disclosure.

FIGS. 5 and 6 illustrate structures of a light emitter 510 and a light receiver 520 of a sensor installed in the electronic device. For example, FIG. 5 is a cross sectional view illustrating a sensor installed in the electronic device, and FIG. 6 is a rear view illustrating a sensor installed in the electronic device.

According to various embodiments, the light emitter 510 can emit light having a set wavelength using a light source or light having different wave lengths by selectively using a plurality of light sources. In various embodiments, the light can be emitted in different combinations of wavelengths, such as an 880 nm wavelength for measuring a heart rate, oxygen saturation, and stress index, 660/880 nm wavelength for measuring a melanin index, 568/660 nm wavelength for measuring an erythema index, and 568/660/880 nm wavelength for measuring a skin tone.

According to various embodiments, the light emitter 510 and the light receiver 520 can be installed at the rear side of the electronic device 101 as shown in FIGS. 5 and 6; however, it is noted the emitter and receiver may be also installed at the front or lateral side of the electronic device 101. Further, the light emitter 510 and the light receiver 520 may not be installed in the electronic device 101 but rather implemented as operably combinable with the electronic device 101 as external accessories.

Figure 7A:
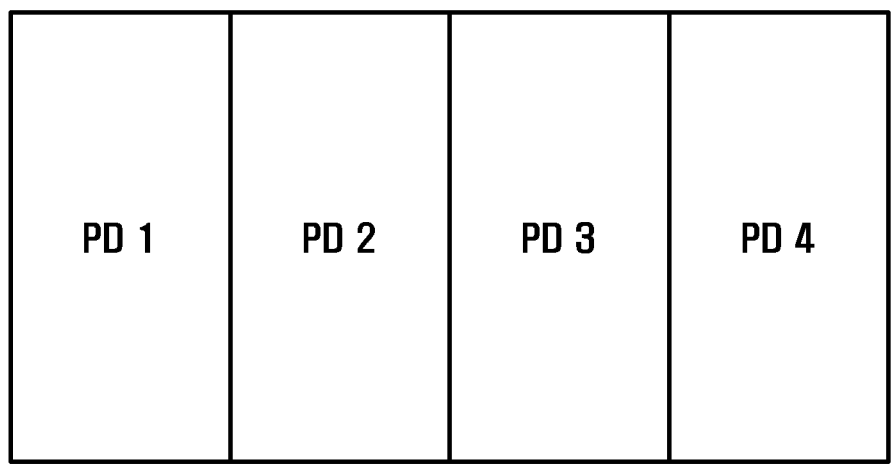
FIG. 7A, FIG. 7B and FIG. 7C are block diagrams illustrating various dispositions of photodiodes included in a light receiver according to various embodiments of the present disclosure.
Figure 7B:
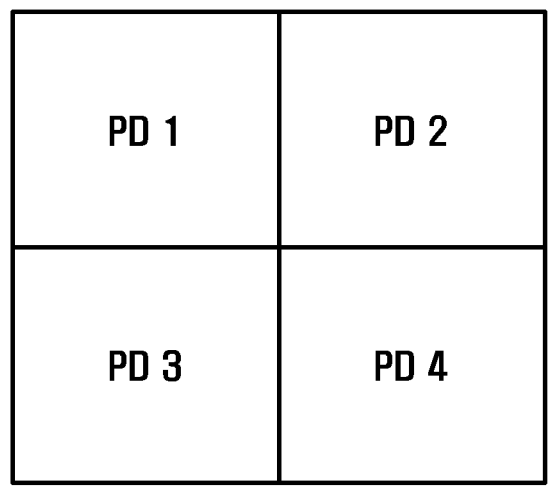
Figure 7C:
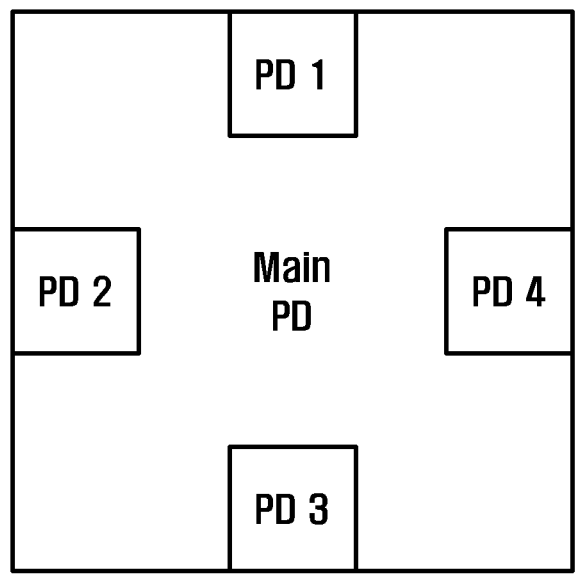

FIGS. 7A to 7C are block diagrams illustrating various dispositions of photodiodes included in a light receiver 520 according to various embodiments of the present disclosure.

According to various embodiments, the electronic device 101 can absorb a reflected light through at least one photodiode (e.g., PD1, PD2, PD3, PD4, and/or a Main PD). For example, the photodiodes can be disposed in a row from the left to the right or from the right to the left as shown in FIG. 7A, in a quadrilateral form as shown in FIG. 7B, or in the center and along the various edges as shown in FIG. 7C. Of course, the invention is not limited to these configurations, and further configurations are possible.

According to various embodiments, the electronic device 101 can identify an inclination extent of a sensor to a skin (e.g., slope information) through a structure of the light emitter 510 having a directionality as shown in FIGS. 7A to 7C. For example, the electronic device 101 can identify an absorption rate and symmetry of reflected light as received by at least one of the photodiodes, and obtain slope information indicating a slope or angle of a plane of the sensor relative to a surface of skin. The electronic device 101 can use the slope information for calculating a skin index. The method for obtaining slope information of a sensor to a skin and calculating a skin index in the sensor of the electronic device 101 according to various embodiments will be described in detail with reference to FIGS. 16 to 18.

Figure 8:
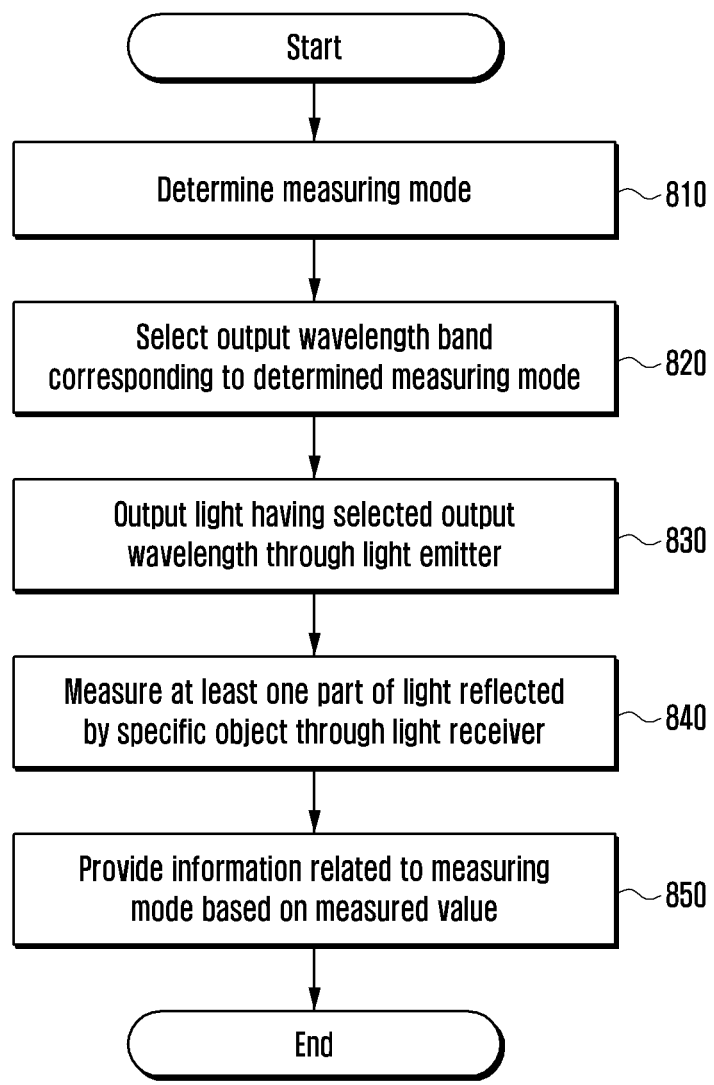
FIG. 8 is a flowchart illustrating a method for determining a measuring mode of a sensor and providing information related to the determined measuring mode in an electronic device according to various embodiments of the present disclosure.

FIG. 8 is a flowchart illustrating a method for determining a measuring mode of a sensor and providing information related to the determined measuring mode in an electronic device according to various embodiments of the present disclosure.

With reference to FIG. 8, the electronic device 101 (e.g., processor 120 of FIG. 1) determines a measuring mode at operation 810. For example, the electronic device 101 can receive a user input for executing a measuring application and determining a measuring mode (e.g., mode for measuring at least one of a heartrate, oxygen saturation, stress index, melanin index, erythema index, and skin tone).

According to various embodiments, the electronic device 101 (e.g., processor 120 of FIG. 1) selects an output wavelength band corresponding to the determined measuring mode at operation 820. For example, the electronic device 101 can select a type of light source and a light amount based on the measuring mode. In some embodiments, the type of measuring mode is pre-associated with the particular output wavelength band or combination of output wavelength bands to be used. Thus, once the user indicates the measuring mode, the pre-associated wavelength or wavelengths can be retrieved.

According to various embodiments, the electronic device 101 (e.g., processor 120 of FIG. 1) controls the output of light having the selected output wavelength (or combined thereof) through a light emitter at operation 830.

According to various embodiments, the electronic device 101 (e.g., processor 120 of FIG. 1) detects and measures at least a portion of the output light as reflected by a specific object (e.g., user's face or wrist) through a light receiver, at operation 840. For example, the light emitted by the light emitter of the electronic device 101 is absorbed, scattered, and/or reflected by a specific object as to be detectable by the light receiver, and the light receiver can therefore measure the scattered or reflected light.

According to various embodiments, the electronic device 101 (e.g., processor 120 of FIG. 1) provides information related to the determined measuring mode at operation 850 based on the light measured by the light receiver. The electronic device 101 can provide not only the resultant values according to the measuring mode (e.g., an estimated heartrate, stress index, melanin index, erythema index, and skin tone, etc.) but also additional information with reference to the resultant values. For example, the electronic device 101 can provide additional information such as ultraviolet exposure, burn hazard, recommended cosmetics, and recommended clothes by considering a user's skin index.

Figure 9:
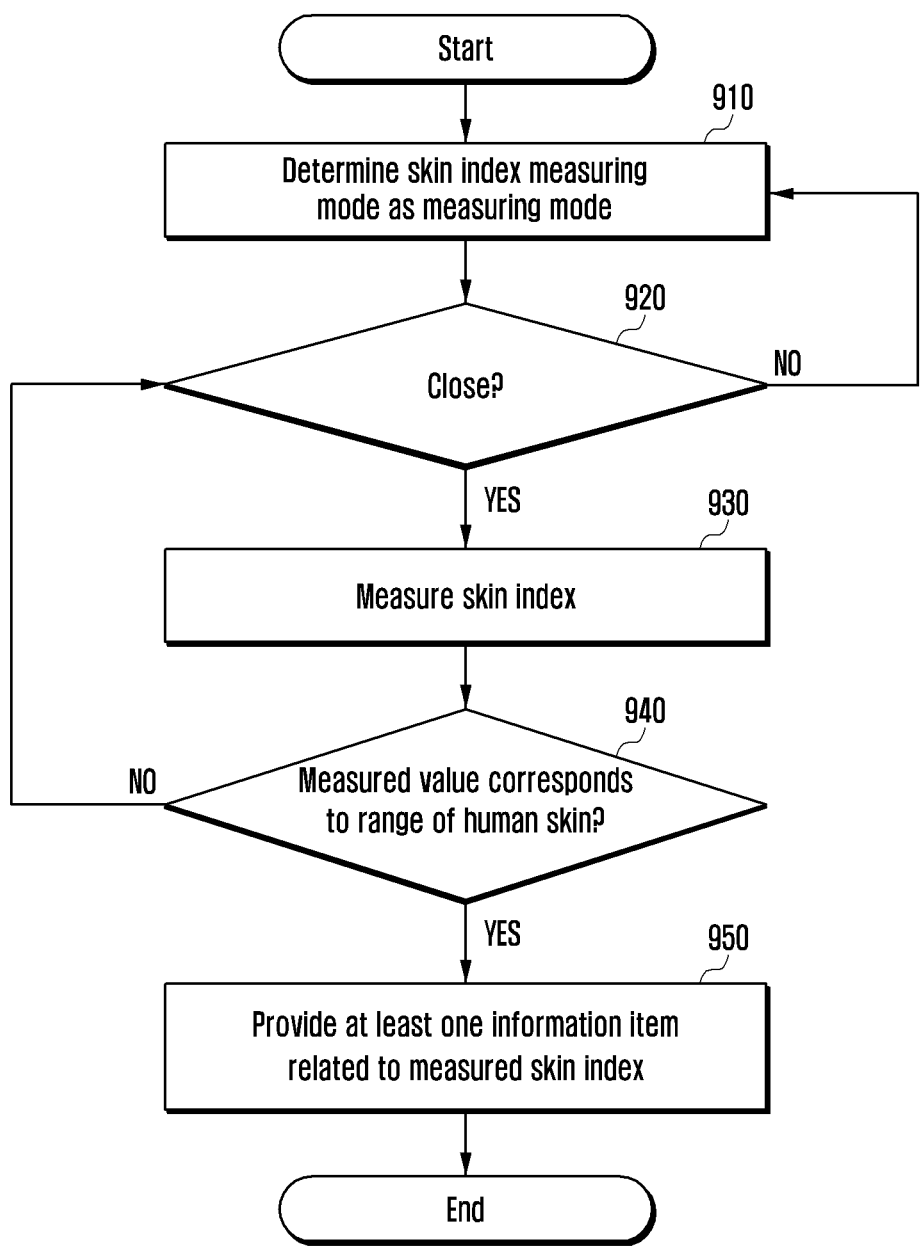
FIG. 9 is a flowchart illustrating a method for providing information related to skin through a sensor in an electronic device according to various embodiments of the present disclosure.

FIG. 9 is a flowchart illustrating a method for providing information related to skin through a sensor in an electronic device according to various embodiments of the present disclosure.

With reference to FIG. 9, the electronic device 101 (e.g., processor 120 of FIG. 1) determines a skin index measuring mode as a measuring mode at operation 910. For example, the skin index measuring mode may be a mode for measuring a user's skin index and providing information related to skin. "Determination" may indicate, for example, detection of activation of the mode or a user-generated request to take a measurement.

According to various embodiments, the electronic device 101 (e.g., processor 120 of FIG. 1) identifies whether a sensor of the electronic device 101 approaches a user's skin at operation 920. According to various embodiments, the operation of the electronic device 101 (e.g., processor 120 of FIG. 1) branches off to operation 910 if the sensor of the electronic device 101 does not approach the user's skin at operation 920. A skin index measurement may be taken upon detection that the distance is, for example, less than or equal to a predetermined distance threshold, qualifying as sufficiently 'close' to get an accurate reading.

According to various embodiments, if the sensor of the electronic device 101 (e.g., processor 120 of FIG. 1) approaches the user's skin at operation 920 to the requisite distance or degree (e.g., "close"), the operation of the electronic device 101 proceeds to operation 930 and controls to measure a skin index. For example, the electronic device 101 can measure at least one skin index (e.g., melanin index, erythema index, and skin tone).

According to various embodiments, the electronic device 101 (e.g., processor 120 of FIG. 1) identifies whether the value measured at operation 930 is disposed within a sampling range indicating the presence of human skin at operation 940. According to various embodiments, if the value measured at operation 930 is not disposed within the range indicating human skin, the operation of the electronic device 101 (e.g., processor 120 of FIG. 1) returns to operation 920 and re-executes identification of whether the sensor of the electronic device 101 has sufficiently approached a threshold distance with the user's skin.

According to various embodiments, if the value measured at operation 930 is disposed in the range indicating the presence of human skin, the operation of the electronic device 101 (e.g., processor 120 of FIG. 1) branches off to operation 950 and provides information related to a skin index. For example, the electronic device 101 may provide information related to the measured skin index and additional information thereof by consideration the measured skin index. For example, information related to an ultraviolet exposure can be provided based on a detected melanin index, skin burn and skin burn hazard can be provided based on a detected erythema index, and information related to cosmetics and clothes suitable for the user can be provided based on a detected skin tone.

Figure 10:
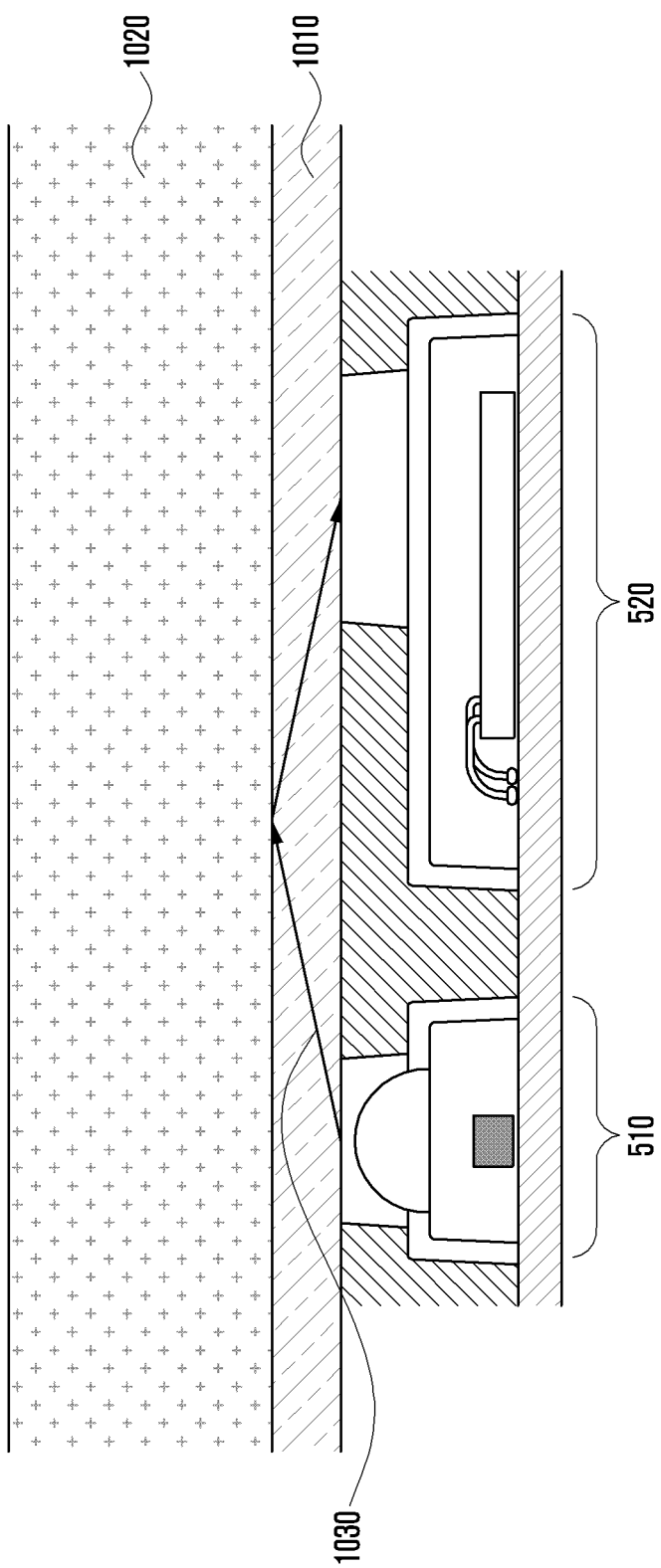
FIG. 10 is a cross sectional view illustrating a method for obtaining information related to skin through a contact measurement in an electronic device according to various embodiments of the present disclosure.

FIG. 10 is a cross sectional view illustrating a method for obtaining information related to skin through a contact measurement in an electronic device according to various embodiments of the present disclosure.

FIG. 10 illustrates a cross sectional view of a sensor (light emitter 510 and light receiver 520; HRM sensor or PPG sensor including a light source; e.g., green LED) and a skin in a state of actively measuring the skin index by placing the electronic device 101 (e.g., terminal glass 1010) on the skin 1020. Because the electronic device 101 is in a state touching the skin 1020, an optical path 1030 may be constant and the skin state may be isolated as the primary factor influencing a value measured by the senor. Accordingly, it can be identified whether a measuring object is a skin, and whether a skin index can be detected by setting a measuring value range indicated by a skin to a threshold. In the meantime, if the contact to the skin is not within the requisite threshold, other factors may influence the measuring value of the sensor and affect, reduce or decrease the accuracy of the measuring value. However, in a general use environment of the electronic device 101, maintaining the electronic device 101 and the user's skin 1020 in a perfect contact state can make it inconvenient for a user to use a measuring function.

Figure 11:
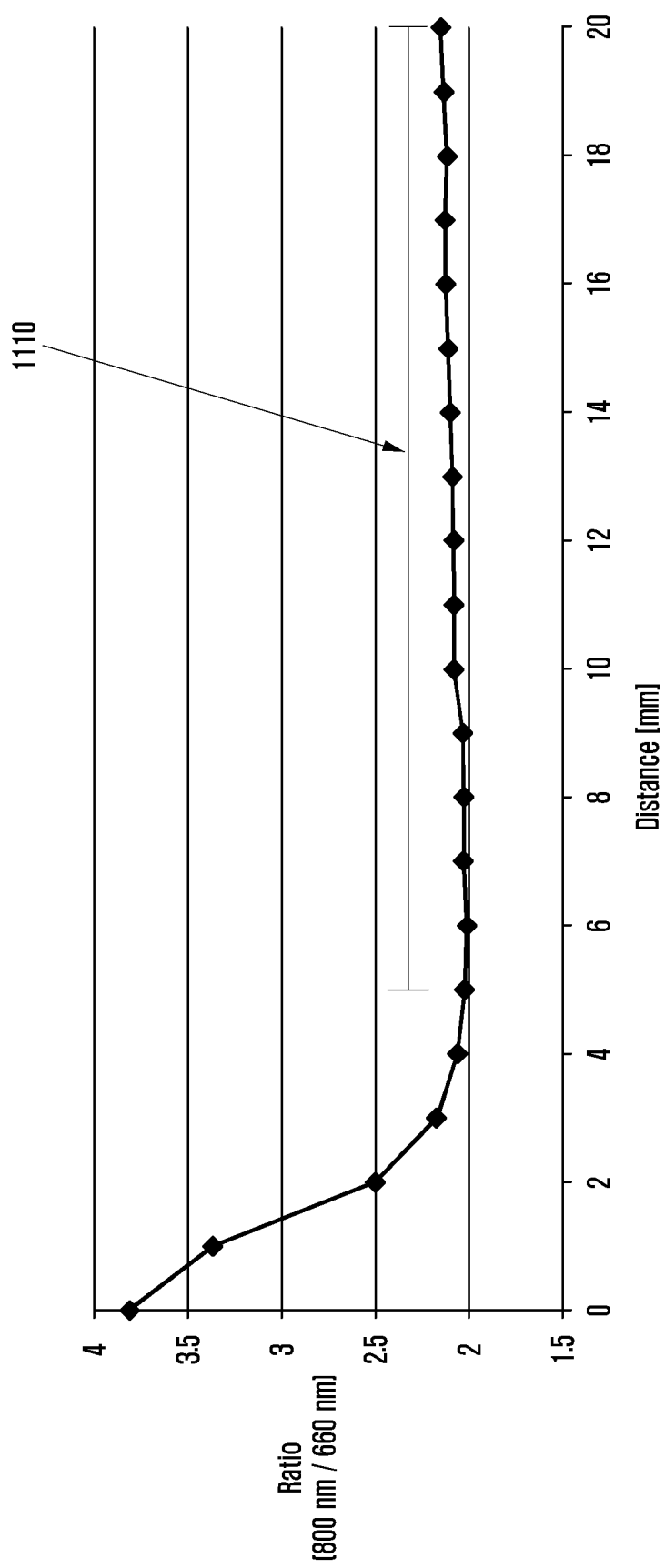
FIG. 11 is a graph illustrating values obtained by a sensor corresponding to a distance between an electronic device and a user's skin according to various embodiments of the present disclosure.

FIG. 11 is a graph illustrating values obtained by a sensor corresponding to a distance between an electronic device and a user's skin according to various embodiments of the present disclosure.

FIG. 11 illustrates a ratio of values measured by a sensor and calculated according to a distance between the electronic device 101 and the user's skin. For example, it can be identified that there is a section 1110 maintaining the ratio according to the distance at a constant value in a specific formula (e.g., dividing a sensor value of a reflected light corresponding to a light source having an 880 nm wavelength by a sensor value of a reflected light corresponding to a light source having a 660 nm wavelength. For example, it can be identified that the ratio according to the distance is maintained at a constant value in a wavelength range 5~20 mm. A melanin index, erythema index, or skin tone can be measured regardless of the distance in a ratio maintaining section 1110, if the specific formula is one of formulas applicable to the melanin index, erythema index, or skin tone. Accordingly, if the electronic device 101 performs a measuring operation at least one time in a section 1110 where a non-contact measurement is possible, the melanin index, erythema index, and skin tone can be measured.

According to various embodiments, the electronic device 101 can perform the non-contact measurement also in a section not included in the ratio maintaining section 1110. According to various embodiments, the electronic device 101 can store a formula related to a skin tone and designed for an infrared (IR) light. Because the infrared light gives the smallest influence to the skin tone, the amount of infrared light reflected by the user's skin can have a relationship with a distance. For example, among various skin tone data corresponding to distance, a formula can be set up by sorting primarily the data having an infrared reflection rate 0.1. Subsequently, if the infrared reflection rate becomes 0.1 when a user measures a skin index in a non-contact method, a skin tone can be identified by applying the measurement values of green and red light to the formula set up for the infrared reflection value 0.1. Similarly, if formulas for infrared reflection values 0.2, 0.3, 0.4, and 0.5 are set up and if any value from 0.1 to 0.5 is received, a user's skin tone can be measured without user's interruption by using a corresponding formula.

Figure 12:
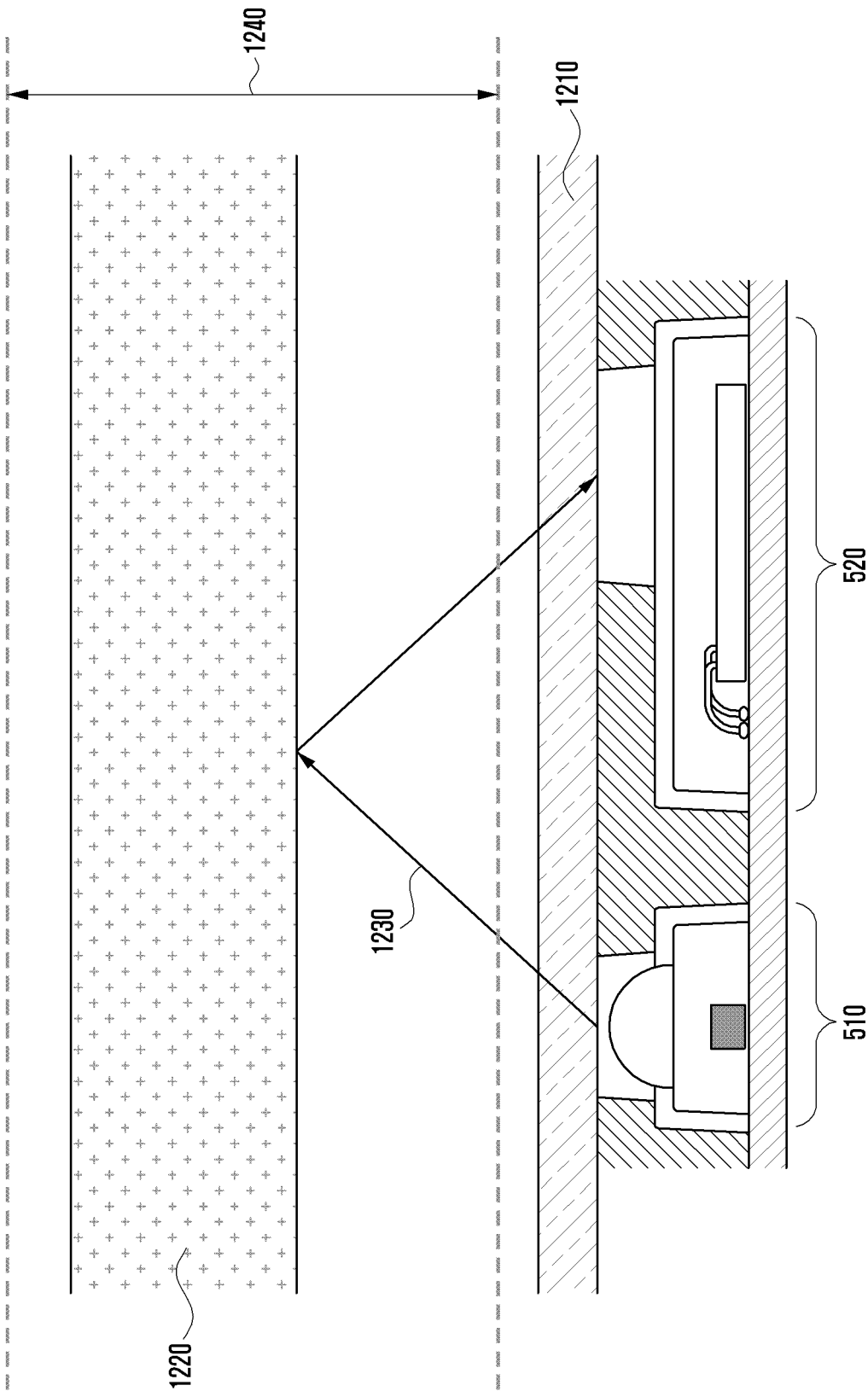
FIG. 12 is a cross sectional view illustrating a method for obtaining information related to skin through a non-contact measurement in an electronic device according to various embodiments of the present disclosure.

FIG. 12 is a cross sectional view illustrating a method for obtaining information related to skin through a non-contact measurement in an electronic device according to various embodiments of the present disclosure.

FIG. 12, illustrates a cross sectional view of a sensor and a skin in case that the electronic device 101 measures a skin index in a state where the user's skin 1220 does not contact a terminal's glass surface 1210. In this case, light emitted by the light emitter 510 is reflected by the user's skin 1220 and absorbed by the light receiver 520 through an optical path 1230.

With reference to FIG. 12, if the electronic device 101 and the user's skin 1220 are located in a ratio maintaining section 1240, the ratio value can be maintained at a specific level regardless of distance, and the skin index can be measured in the ratio maintaining section 1240.

In case of a non-contact measurement, the electronic device 101 and the skin do not contact each other; therefore, it may be more sanitary. Although discrepancies in the position of the skin may arise due to movement or unsteadiness of a user's hand, the accuracy of a measured value can be improved by compensating for the measured value.

FIG. 13 illustrates a method for performing a non-contact measurement in an electronic device according to various embodiments of the present disclosure.

With reference to FIG. 13, at reference number 1310, the electronic device 101 can receive an input of a key, button, and voice for starting a measurement from a user, and approach a measuring object. Here, the electronic device 101 may not directly contact a user's skin and may come close to the user's skin in the ratio maintaining section 1110 (i.e., of FIG. 11).

According to various embodiments, at reference number 1320, the electronic device 101 can be located close to the user's skin in the ratio maintaining section. If the electronic device 101 is located in the ratio maintaining section, the electronic device can measure a skin index as much as a predetermined number or for a predetermined time. According to various embodiments, the electronic device 101 can inform a helpful content for performing a non-contact measurement to the user. For example, in case of performing a non-contact measurement, the electronic device 101 can output a text, image, sound, or vibration so that the user can maintain a specific distance range. Further, the electronic device 101 can inform a remaining measuring time or number of times to the user until the non-contact measurement becomes complete.

According to various embodiments, at reference number 1330, the electronic device 101 can inform the user that the skin index measurement is complete. For example, by using at least one of an indication, sound, and vibration, the electronic device 101 can inform the user that the measurement is complete. Subsequently, the electronic device 101 can display information related to a measurement result in the display 160, and the user can identify the information related to a measurement result by displacing the electronic device 101 from the user's skin.

According to various embodiments, the electronic device 101 can use a method of calculating an average value from a plurality of data obtained in a specific distance range in order to improve the accuracy of the non-contact measurement.

Figure 14:
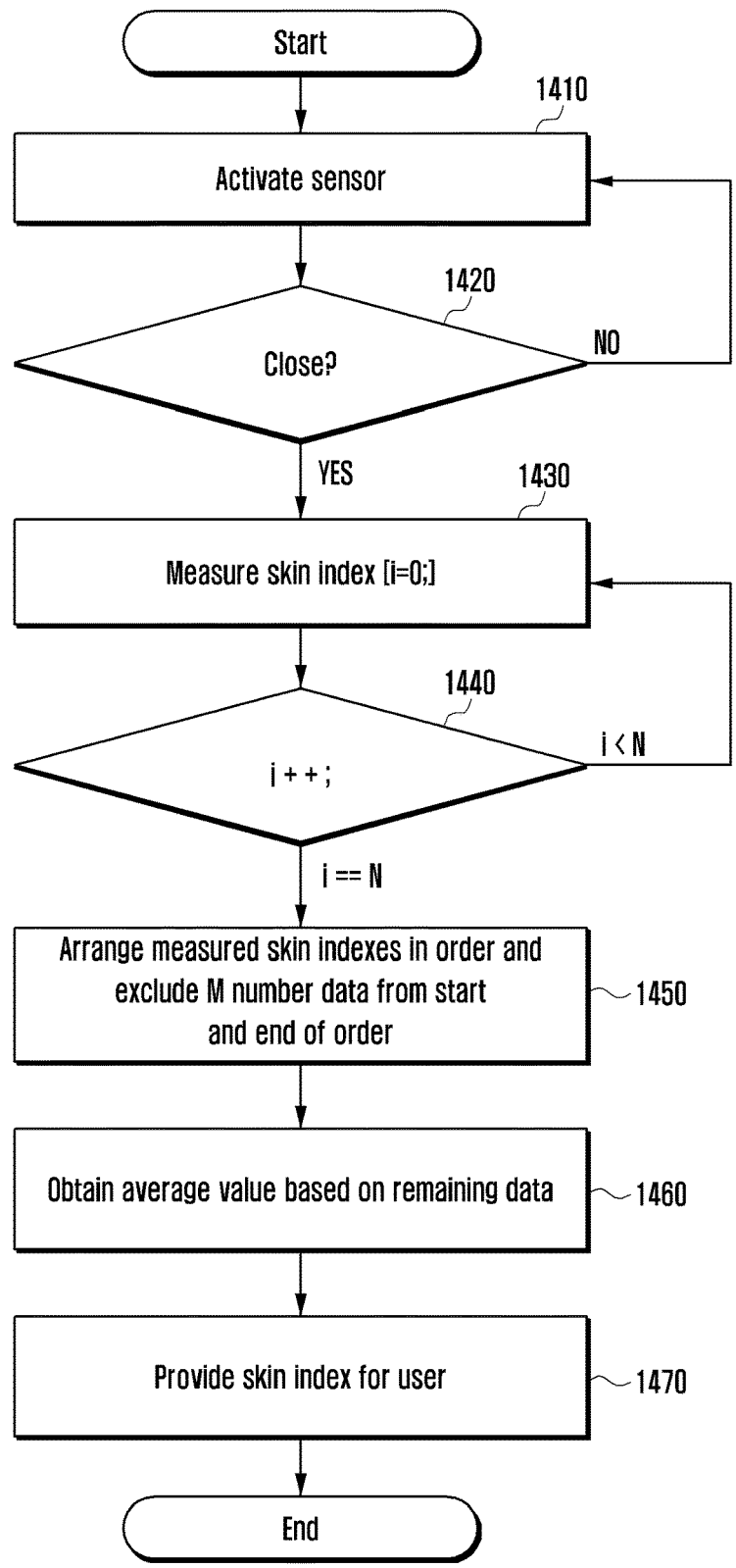
FIG. 14 is a flowchart illustrating a method for performing a non-contact measurement in an electronic device according to various embodiments of the present disclosure.

FIG. 14 is a flowchart illustrating a method for performing a non-contact measurement in an electronic device according to various embodiments of the present disclosure.

With reference to FIG. 14, the electronic device 101 (e.g., processor 120 of FIG. 1) activates a sensor to measure at least one skin index at operation 1410.

According to various embodiments, the electronic device 101 (e.g., processor 120 of FIG. 1) identifies whether a user's skin is within a threshold distance of the sensor of the electronic device 101 at operation 1420. If the user's skin does not come within the threshold distance to the sensor of the electronic device 101, the operation of the electronic device returns to operation 1410 to reattempt detection of a user's skin.

According to various embodiments, if the user's skin is identified as being within the threshold distance of the sensor of the electronic device 101 (e.g., processor 120 of FIG. 1), the electronic device 101 measures the user's skin index a predetermined number of times through operations 1430 and 1440. For example, the electronic device 101 can measure the user's skin index a total of 14 times (e.g., N=14), through an iterative loop as seen in operations 1430 and 1440.

According to various embodiments, the electronic device 101 (e.g., processor 120 of FIG. 1) arranges skin index measurement values in a specific order and excludes a predetermined number (M) of the measurement values from the start and end of the order at operation 1450. For example, if M equals 4, the electronic device 101 can exclude 8 measurement values by excluding 4 measurement values from the start of the order and 4 measurement values from the end of the order.

According to various embodiments, the electronic device 101 (e.g., processor 120 of FIG. 1) obtains an average value of skin index from the remaining measurement values at operation 1460. For example, the electronic device 101 can obtain an average value for the 6 remaining measurement values by excluding the 8 measurement values from the total of the 14 detected measurement values.

According to various embodiments, at operation 1470, the electronic device 101 (e.g., processor 120 of FIG. 1) provides the average value obtained at operation 1460 as a detected user's skin index.

Figure 15:
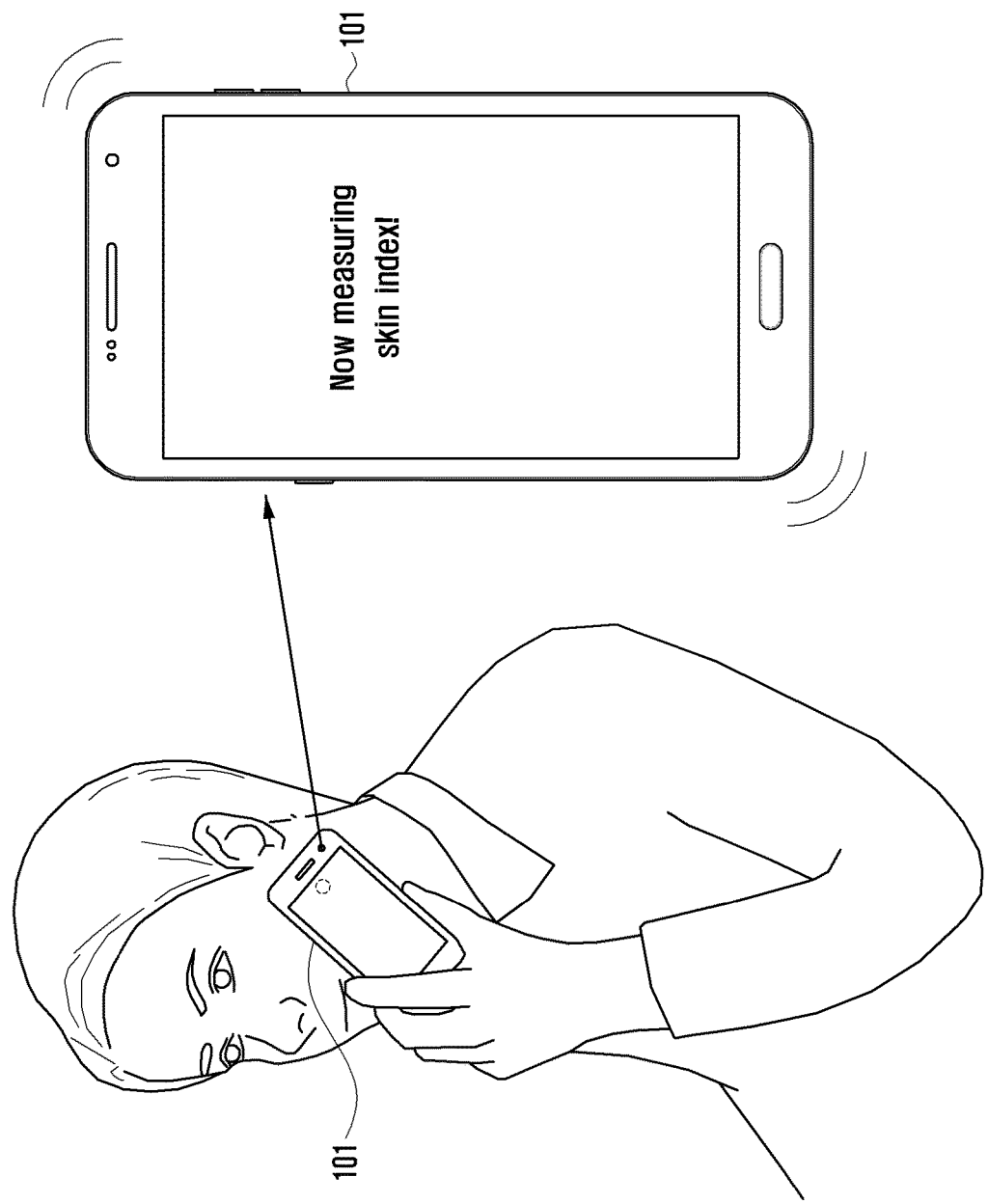
FIG. 15 illustrates a method for providing information related to a skin measurement for a user when measuring the information related to skin in an electronic device according to various embodiments of the present disclosure.

FIG. 15 illustrates a method for providing information related to a skin measurement for a user when measuring the information related to skin in an electronic device according to various embodiments of the present disclosure.

With reference to FIG. 15, if the skin-related information is measured by a sensor, the electronic device 101 can inform a measurable distance and completion of measurement to the user by outputting at least one of a text, image, sound, and vibration.

Figure 16:
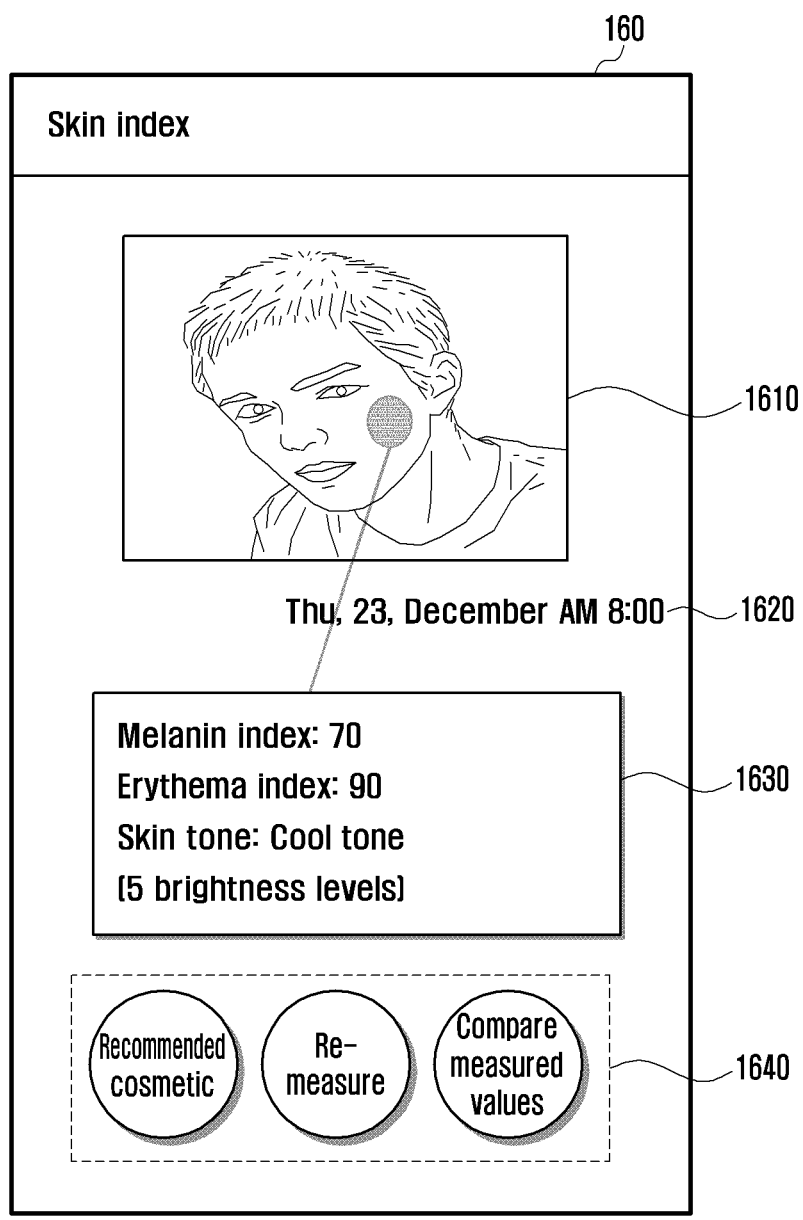
FIG. 16 illustrates a method for providing information related to skin in an electronic device according to various embodiments of the present disclosure.

FIG. 16 illustrates a method for providing information related to skin in an electronic device according to various embodiments of the present disclosure.

With reference to FIG. 16, the electronic device 101 can output the measured skin index to the display through a user interface (UI).

According to various embodiments, the electronic device 101 can provide a user profile 1610, measuring time 1620, measuring index 1630, and menu option 1640 through the user interface. For example, the menu option 1640 may include selectable options such as at least one of a recommended clothes, recommended cosmetics, user's skin type, cautions for the corresponding skin type, re-measurement, comparison of measurement values, and notice to a friend. Further, when recommending clothes and cosmetics, the electronic device 101 can provide a user interface to facilitate the requisite functions thereof (e.g., an interface for searching for a lowest price of corresponding product, retrieving information related to an online or offline store selling the corresponding product, and executing online purchase) so that the user can find and purchase a corresponding product.

Figure 17A:
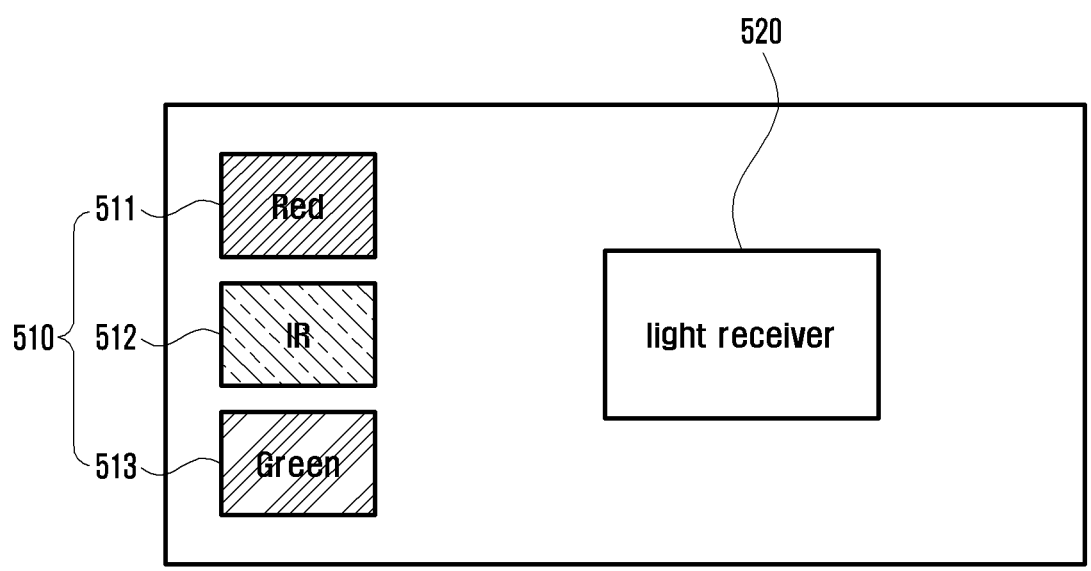
FIG. 17A illustrates structures of a light emitter and a light receiver of a sensor installed in an electronic device according to various embodiments of the present disclosure.

FIG. 17A illustrates structures of a light emitter and a light receiver of a sensor installed in an electronic device according to various embodiments of the present disclosure.

With reference to FIG. 17A, the light sources 511, 512, and 513 of the light emitter 510 can be disposed asymmetrically to the light receiver 520. For example, in an arrangement of the three light sources 511, 512 and 513 the red light source 511 may be located at a top terminal end of the arrangement compared with the light receiver 520, and the green light source 513 may be located at a bottom terminal end of the arrangement compared with the light receiver 520. However, the infrared light source 512 may be disposed symmetrically horizontal on a similar or same axis with the light receiver 520. Accordingly, absorption rates of different photodiodes (refer to FIG. 7A to 7C) of the light receiver 520 can be distinguished through the infrared light source 512, and parallel or slope information between the electronic device 101 and the user's skin can be identified.

Figure 17B:
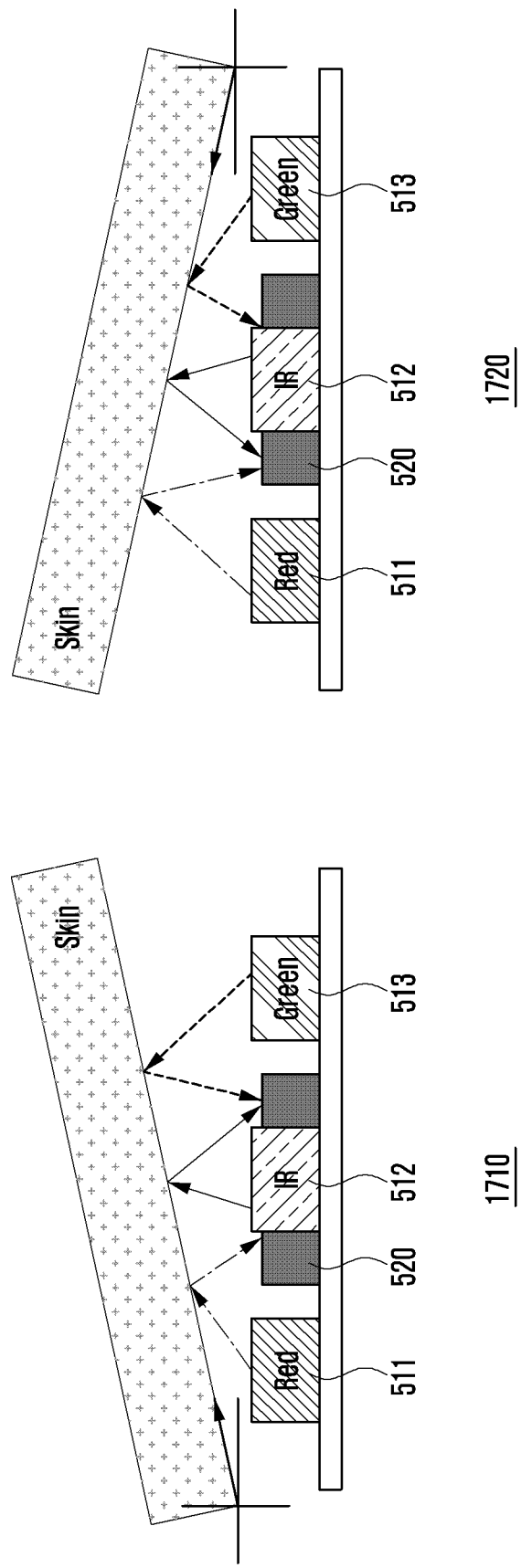
FIG. 17B illustrates an optical path in case that a sensor installed in an electronic device and a user's skin are nonparallel to each other according to various embodiments of the present disclosure.

FIG. 17B illustrates an optical path in case that a sensor installed in an electronic device and a user's skin are nonparallel to each other according to various embodiments of the present disclosure.

With reference to FIG. 17B, if a slope is formed between the electronic device 101 and the user's skin, optical paths from the light sources 511, 512, and 513 to the light receiver 520 may differ (refer to reference numbers 1710 and 1720). Accordingly, there may be difficulties in correctly measuring a melanin index, erythema index, and skin tone. However the skin index can be measured correctly by using a method illustrated in FIG. 18.

Figure 18:
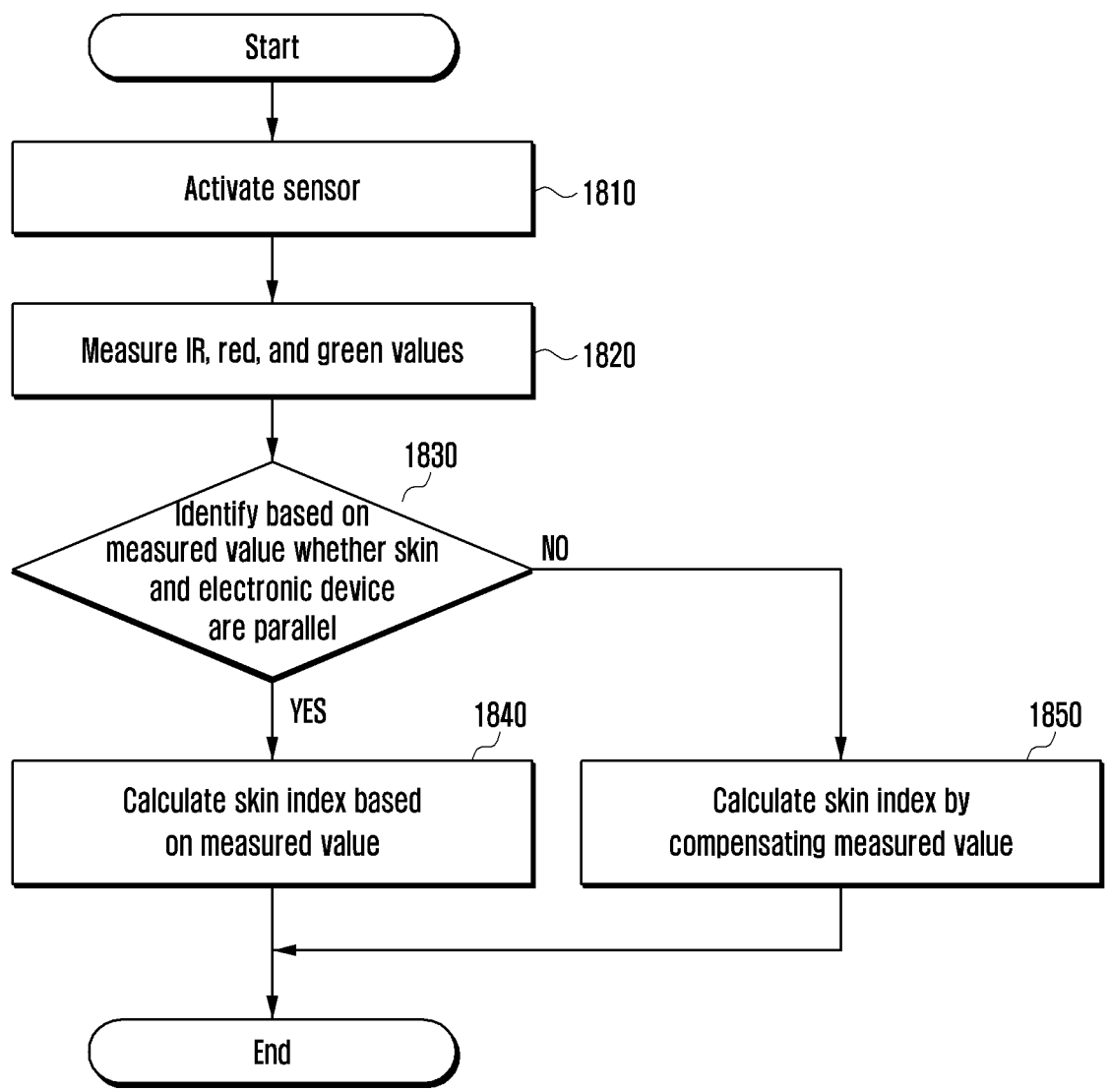
FIG. 18 is a flowchart illustrating a method for calculating information related to skin by considering a case that a sensor installed in an electronic device and a user's skin are parallel or nonparallel to each other according to various embodiments of the present disclosure.

FIG. 18 is a flowchart illustrating a method for calculating information related to skin by considering cases that a sensor installed in an electronic device and a user's skin are parallel or nonparallel to each other according to various embodiments of the present disclosure.

With reference to FIG. 18, the electronic device 101 (e.g., processor 120 of FIG. 1) activates a sensor to measure a skin index at operation 1810.

According to various embodiments, the electronic device 101 (e.g., processor 120 of FIG. 1) measures at least one portion of light emitted by at least one light source (e.g., infrared, red, and/or green light) and reflected by a user's skin through a light receiver at operation 1820.

According to various embodiments, at operation 1830, the electronic device 101 (e.g., processor 120 of FIG. 1) identifies whether the electronic device 101 and the user's skin are disposes as to be parallel to one another based on the values measured at operation 1820.

According to various embodiments, if the electronic device 101 and the user's skin are disposed parallel relative to one another as confirmed in at operation 1830, the operation of the electronic device 101 (e.g., processor 120 of FIG. 1) proceeds to operation 1840 and calculates a skin index based on the measured values.

According to various embodiments, if the electronic device 101 and the user's skin are disposed nonparallel to one another at operation 1830, the operation of the electronic device 101 (e.g., processor 120 of FIG. 1) proceeds to operation 1850 and calculates a skin index by compensating the measured value to produce a more accurate reading. For example, if the electronic device 101 and the user's skin are disposed nonparallel to one another, the electronic device 101 can compensate for the infrared, red, and green values by comparing values input through each photodiode of the light receiver.

According to various embodiments with reference to FIGS. 7A to 7C, the electronic device 101 (e.g., processor 120 of FIG. 1) can identify that amounts of infrared (IR) light input through the PD1, PD2, PD3, and PD4 are asymmetrical or different. In this case, slope information between the electronic device and the user's skin can be identified by matching with a look-up table, which is prepared by measuring the amount of infrared light with a standard reflection material or a grey scale for each slope. The electronic device 101 can compensate the measured value by comparing a value measured at a corresponding slope and a value measured in a parallel state. Through this slope compensation, the degree of freedom and usability in the structure and disposition can be improved, in contrast with the general color measurement equipment that utilizes a symmetrical disposition between a light emitter and a light receiver. Further, the reliability of a product can be increased by improving the accuracy of measured values through the compensation.

In the meantime, according to various embodiments, the electronic device 101 (e.g., processor 120 of FIG. 1) can control to calculate skin-related information when the sensor and the user's skin are located parallel without the above compensation.

Figure 19B:
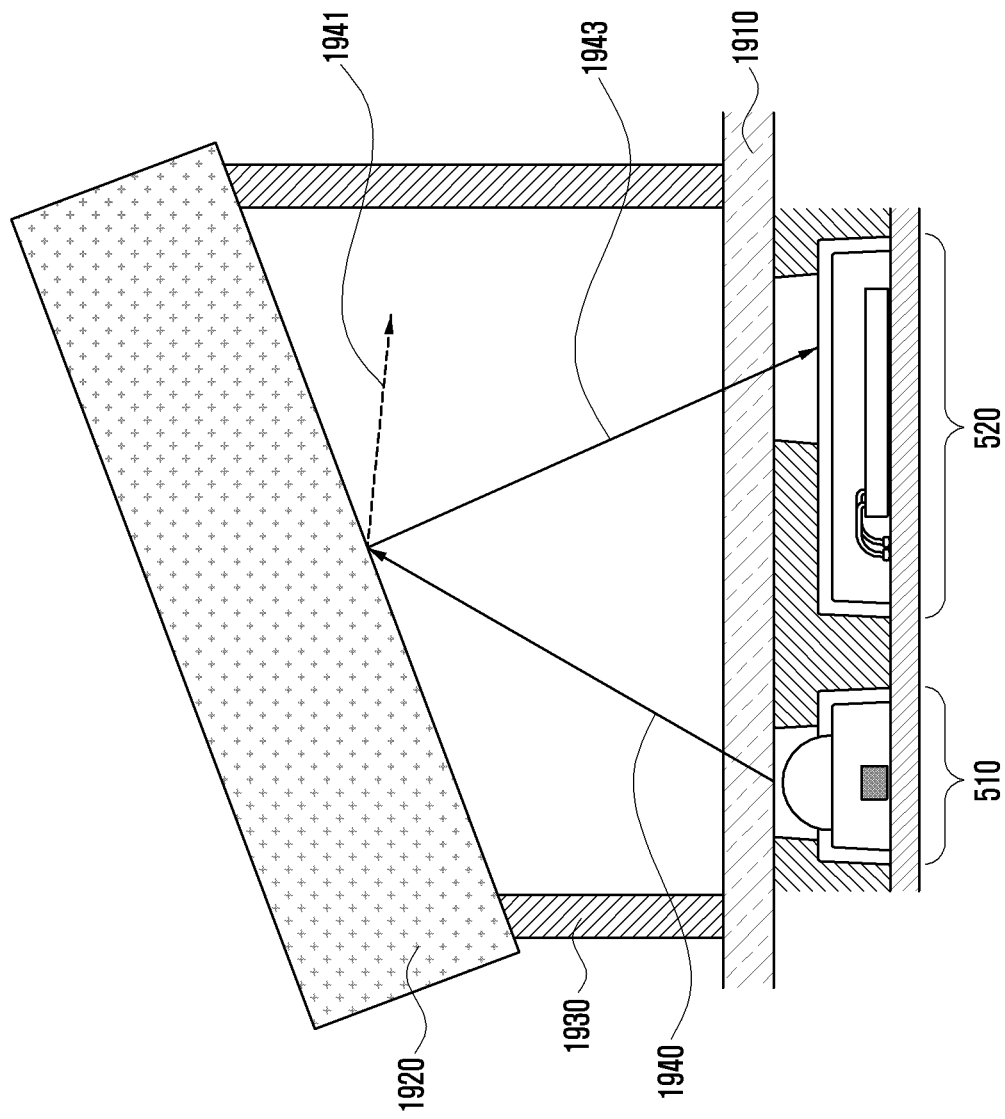
Figure 19C:
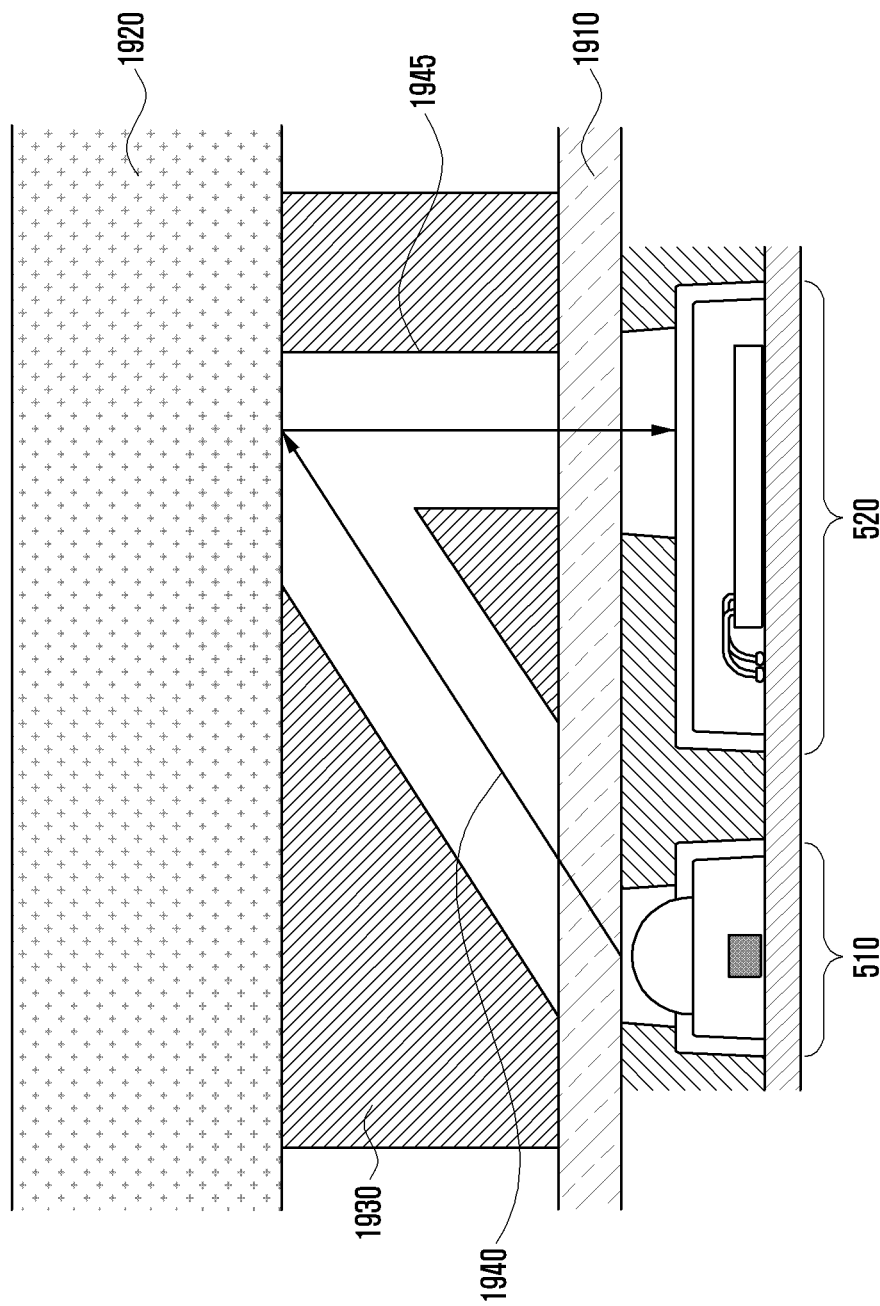

FIGS. 19A to 19C are cross sectional views illustrating a method for measuring information related to skin by attaching an external accessory to an electronic device according to various embodiments of the present disclosure.

With reference to FIG. 19A, the skin-related information can be measured when an external accessory 1930 is disposed between the electronic device 101 (e.g., glass 1910) and a user's skin 1920. For example, an expected measuring distance may change because of the attachment of a phone case to a smartphone implementing the sensors. In this case, a separate optical path 1940 component may be formed besides light reflected by the skin 1920. A measurement value of the separate optical path 1940 component may be the same regardless of the measurement object such as a skin 1920. Accordingly, the electronic device 101 can identify that the external accessory 1930 is attached if a value of the separate optical path 1940 component is measured after starting the measurement. If the attachment of the external accessory 1930 is identified, the electronic device 101 can improve the accuracy of skin index measurement by applying a separate or different algorithm relative to the standard one.

With reference to FIG. 19B, the electronic device 101 can receive the diffuse reflection component 1943 by excluding a regular reflection component 1941 (e.g., an incident angle and a reflection angle against a skin are equal) through the optical path. The reason for excluding a regular reflection component 1941 is that the regular reflection component mostly includes information of the light source itself, and possesses insufficient information pertaining to the skin as a reflection object.

According to various embodiments, the electronic device 101 can measure a skin index by attaching an external accessory in order to receive the diffuse reflection component 1943. For example, the regular reflection component 1941 can be removed by forming a slope in the external accessory 1930. Like this, the diffuse reflection component 1943 can be measured by the light receiver 520 of the electronic device 101.

With reference to FIG. 19C, the electronic device 101 can receive the diffuse reflection component (e.g., separate optical path) 1940 by attaching an external accessory 1930. For example, the regular reflection component can be removed by the disposition of a structure or pathway 1945, which limits the procession of the optical path in the external accessory 1930.

Figure 20:
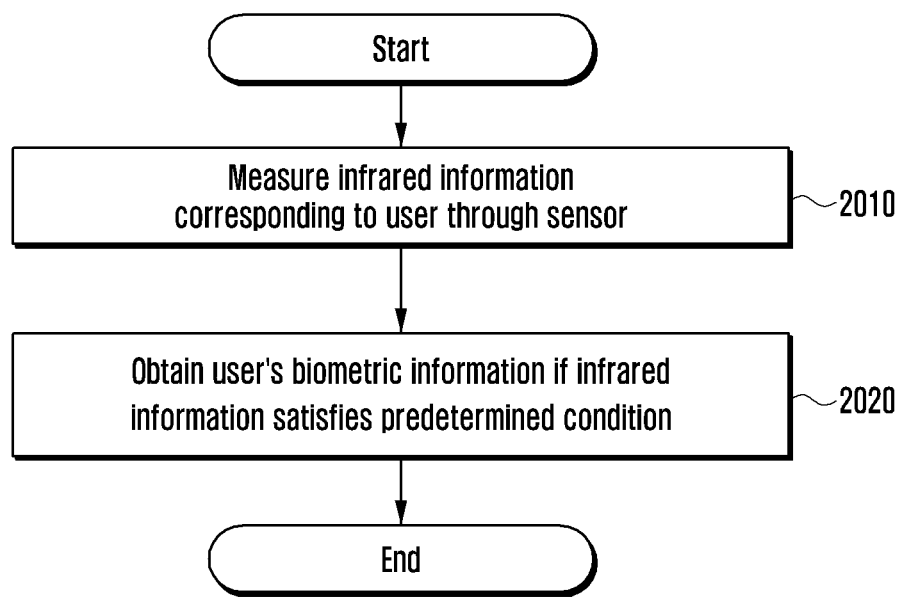
FIG. 20 is a flowchart illustrating a method for obtaining a user's biometric information in an electronic device according to various embodiments of the present disclosure.

FIG. 20 is a flowchart illustrating a method for obtaining a user's biometric information in an electronic device according to various embodiments of the present disclosure.

With reference to FIG. 20, the electronic device 101 measures infrared information corresponding to a user through a sensor at operation 2010. For example, the infrared information may mean information related to an infrared light emitted by the electronic device 101 reaching a user, being reflected by the user, and coming back to the electronic device 101. Generally, the infrared light has a wavelength giving a small influence to a skin tone. Accordingly, a relationship can be established according to a distance between the user and the electronic device 101 based on a value of the infrared light reflected by a skin.

According to various embodiments of the present disclosure, if the infrared information satisfies a predetermined condition, the electronic device 101 obtains a user's biometric information at operation 2020. For example, the biometric information may include at least one of a melanin index, erythema index, and skin tone.

According to various embodiments of the present disclosure, the predetermined condition may include a case that the infrared information is included in a predetermined value range. For example, if the infrared information is included in the predetermined value range, it may mean that a user's skin is located within a predetermined distance range (e.g., reference number 1110 of FIG. 11) from the electronic device 101.

According to various embodiments of the present disclosure, if the infrared information is included in the predetermined value range, the electronic device 101 can measure sensor information corresponding to at least two light sources (e.g., a light source having an 880 nm wavelength and another light source having a 660 nm wavelength).

According to various embodiments of the present disclosure, if the infrared information is included in the predetermined value range, a ratio between sensor information of a first light source (e.g., 880 nm wavelength, infrared (IR) light, reference number 512 of FIG. 17A) and sensor information of a second light source (e.g., 660 nm wavelength, red light, reference number 511 of FIG. 17A) can remain at a specific level without differences of ratio value according to distance (i.e., dividing a sensor value of a reflected light corresponding to a light source having an 880 nm wavelength by a sensor value of a reflected light corresponding to a light source having a 660 nm wavelength). The sensor information of the first light source and the sensor information of the second light source are not limited to the above embodiment, and the light sources can be replaced variously in order to obtain a user's biometric information.

According to various embodiments of the present disclosure, the sensor of the electronic device 101 may include light emitters 410 and 510 and light receivers 420 and 520. For example, the light receiver may include a plurality of photodiodes (PDs) disposed as shown in FIGS. 7A to 7C according to various embodiments.

An electronic device according to various embodiments of the present disclosure may comprise a sensor and a processor. The processor may be configured to measure infrared information corresponding to a user through the sensor and to obtain the user's biometric information if the infrared information satisfies a predetermined condition.

The predetermined condition may include a case that the infrared information is included in a predetermined value range.

The sensor may include a plurality of light sources, and the processor may be configured to measure sensor information corresponding to at least two light sources among the plurality of light sources if the infrared information is included in a predetermined value range and to obtain the user's biometric information based on the sensor information corresponding to at least two light sources.

The sensor information corresponding to at least two light sources may include first light source sensor information and second light source sensor information. A ratio of the first light source sensor information to the second light source sensor information can be maintained at a specific level if the infrared information is included in a predetermined value range.

The processor may be configured to obtain information related to the parallelism between the sensor and the user based on the infrared information and to obtain the user's biometric information based on the information related to the parallelism.

The sensor may include a light emitter and a light receiver, the light emitter may include a light source emitting an infrared light, and the light receiver may include a plurality of photodiodes (PDs). The processor may be configured to obtain the information related to the parallelism based on the symmetry of infrared information measured by the plurality of photodiodes.

The processor may be configured to compensate a value measured by the sensor if the sensor and the user are in a nonparallel state and to obtain the user's biometric information based on the compensation.

The biometric information may include at least one of a melanin index, an erythema index, and a skin tone.

The electronic device may be configured to combine with an external accessory, and light emitted by the sensor is diffused and reflected by the user based on the combination.

The external accessory combined with the electronic device may be configured to have a slope structure at an outer surface or an internal structure limiting an optical path.

A method for providing information related to skin in an electronic device according to various embodiments of the present disclosure may include measuring infrared information corresponding to a user through a sensor and obtaining the user's biometric information if the infrared information satisfies a predetermined condition.

The predetermined condition may include a case that the infrared information is included in a predetermined value range.

The sensor may include a plurality of light sources. The method may further include the operations of measuring sensor information corresponding to at least two light sources among the plurality of light sources if the infrared information is included in a predetermined value range and obtaining the user's biometric information based on the sensor information corresponding to at least two light sources.

The sensor information corresponding to at least two light sources may include first light source sensor information and second light source sensor information. A ratio of the first light source sensor information to the second light source sensor information can be maintained at a specific level if the infrared information is included in a predetermined value range.

The method may further include the operations of obtaining information related to the parallelism between the sensor and the user based on the infrared information and obtaining the user's biometric information based on the information related to the parallelism.

The sensor may include a light emitter and a light receiver, the light emitter may include a light source emitting an infrared light, and the light receiver may include a plurality of photodiodes (PDs). The method may further include the operation of obtaining the information related to the parallelism based on the symmetry of infrared information measured by the plurality of photodiodes.

The method may further include the operations of compensating a value measured by the sensor if the sensor and the user are in a nonparallel state and obtaining the user's biometric information based on the compensation.

The biometric information may include at least one of a melanin index, an erythema index, and a skin tone.

The electronic device may be configured to combine with an external accessory, and light emitted by the sensor is diffused and reflected by the user based on the combination.

The external accessory combined with the electronic device may be configured to have a slope structure at an outer surface or an internal structure limiting an optical path.

According to various embodiments of the present disclosure, an electronic device can provide skin-related information as well as functions provided by a pre-installed sensor through structure modification of the pre-installed sensor (e.g., heart rate monitor (HRM) sensor or photoplethysmogram (PPG) sensor). For example, the electronic device can provide information of a melanin index, erythema index, and skin tone based on visible light (e.g., red and green light) and infrared (IR) light information. In particular, by using the pre-installed sensor, a design change for adding a skin measuring sensor or forming a hole may be unnecessary.

The term "module" used in the present disclosure may refer to a unit including one or more combinations of hardware, software, and firmware. The "module" may be interchangeable with a term, such as "unit," "logic," "logical block," "component," or "circuit". The "module" may be a minimum unit of a component formed as one body or a part thereof, may be a minimum unit for performing one or more functions or a part thereof, and may be implemented mechanically or electronically. For example, the "module" according to an embodiment of the present disclosure may include at least one of an application-specific integrated circuit (ASIC) chip, a field-programmable gate array (FPGA), and a programmable-logic device for performing certain operations which have been known or are to be developed in the future.

Examples of computer-readable media include: magnetic media, such as hard disks, floppy disks, and magnetic tape; optical media such as compact disc read only memory (CD-ROM) disks and digital versatile disc (DVD), magneto-optical media, such as floptical disks, and hardware devices that are specially configured to store and perform program instructions, such as ROM, RAM, and flash memory. Examples of program instructions include machine code instructions created by assembly languages, such as a compiler, and code instructions created by a high-level programming language executable in computers using an interpreter. The described hardware devices may be configured to act as one or more software modules in order to perform the operations and methods described above, or vice versa.

Modules or programming modules according to the embodiments of the present disclosure may include one or more components, remove part of the components described above, or include new components. The operations performed by modules, programming modules, or the other components, according to the present disclosure, may be executed in serial, parallel, repetitive or heuristic fashion. Part of the operations can be executed in any other order, omitted, or executed with additional operations.

Although embodiments of the disclosure have been described in detail above, it should be understood that many variations and modifications of the basic inventive concept herein described, which may be apparent to those skilled in the art, will still fall within the embodiments of the disclosure as defined in the appended claims.

What is claimed is:

1. An electronic device comprising:
   a sensor configured to emit light and receive reflected light to detect at least distance of the electronic device from a user, and skin-related biometric information; and
   a processor,
   wherein the processor is configured to:
   using the sensor, emit infrared light toward the user and receive the infrared light when reflected off the user, and
   detect whether the electronic device is within a threshold distance of the user, by determining whether the received infrared light satisfies a predetermined condition via comparison against a predetermined value range,
   based on detecting that the received infrared light satisfies the predetermined condition indicating the user is within a threshold distance of the electronic device, detect, using the sensor, biometric information of the user,
   wherein the biometric information includes at least one of a melanin index, an erythema index, and a skin tone, and
   wherein the processor is further configured to:
      identify, in a specific distance range between the electronic device and the user, a ratio of a first light source sensor information corresponding to the first light source and a second light source sensor information corresponding to the second light source that maintains a constant value, wherein the ratio is related to the biometric information, and
      measure the biometric information using the ratio based on a distance between the electronic device and the user within the specific distance.

2. The electronic device of claim 1, wherein detecting the biometric information further comprises:
   after detecting that the received infrared light satisfies the predetermined condition, detecting whether the received infrared light is disposed in a sampling range indicating human skin,
   wherein the biometric information of the user is detected based on detecting that the received infrared light is disposed in the sampling range.

3. The electronic device of claim 2, wherein the sensor comprises a plurality of light sources, the processor further configured to:
   analyze sensor information corresponding to at least a first light source and a second light source of the plurality of light sources if the received infrared light is included in the predetermined value range, and
   detecting the biometric information based on the analyzed sensor information.

4. The electronic device of claim 1, wherein the processor is configured to:
   store a plurality of measuring modes in memory, each measuring mode corresponding to at least one wavelength band; and
   prior to emitting the infrared light, detect an input selecting a measuring mode from among the plurality of measuring modes, and retrieve, based on the selected measuring mode, at least one output wavelength band pre-associated with the selected measuring mode from the memory,
   wherein the infrared light is emitted at the selected at least one output wavelength band to acquire a desired type of the biometric information.

5. The electronic device of claim 4, wherein the sensor comprises a light emitter and a light receiver, the light emitter including a light source emitting the infrared light, and the light receiver including a plurality of photodiodes (PDs), and
   wherein detecting whether the sensor is disposed parallel to a skin surface is based at least partially on symmetry of the received infrared light, as received by the plurality of photodiodes.

6. The electronic device of claim 5, wherein when the infrared light indicates that the sensor is disposed nonparallel to the skin surface, the processor is further configured to apply compensation to a value received by the sensor, and detect the biometric information using the compensated value.

7. The electronic device of claim 1, wherein the sensor is further configured to detect, in addition to skin-related biometric information and distance, heart-related biometric information, using emission and reception of light, and
   wherein the sensor is configured to detect the skin-related biometric information, distance and heart-related biometric information by adjusting a wavelength of light emitted and received by the sensor.

8. The electronic device of claim 1, wherein the sensor further comprises a light emitter that emits the infrared light subsequently received by the sensor, and
   wherein the electronic device is interoperable with an external accessory, and at least a portion of the infrared light emitted by the sensor is diffused and reflected by the external accessory.

9. The electronic device of claim 8, wherein the external accessory includes a surface possessing a slope relative to the electronic device when disposed adjacent to the electronic device, and an internal cavity defining an optical path through which the infrared light travels when emitted to be detected by the sensor.

10. A method in an electronic device, the method comprising:
   using a sensor configured to emit light and receive reflected light, emitting infrared light toward the user and receiving the infrared light when reflected off the user;
   detecting, by a processor, whether the electronic device is within a threshold distance of the user, by determining whether the received infrared light satisfies a predetermined condition via comparison against a predetermined value range; and
   based on detecting that the received infrared light satisfies the predetermined condition indicating the user is in the threshold distance of the electronic device, detecting, using the sensor, biometric information of the user,
   wherein the biometric information includes at least one of a melanin index, an erythema index, and a skin tone,
   wherein detecting the biometric information further comprises:
      identifying, in a specific distance range between the electronic device and the user, a ratio of a first light source sensor information corresponding to the first light source and a second light source sensor information corresponding to the second light source that maintains a constant value, wherein the ratio is related to the biometric information, and measuring the biometric information using the ratio based on a distance between the electronic device and the user within the specific distance.

11. The method of claim 10, wherein detecting the biometric information further comprises:

after detecting that the received infrared light satisfies the predetermined condition, detecting whether the received infrared light is disposed in a sampling range indicating human skin, wherein the biometric information of the user is detected based on detecting that the received infrared light is disposed in the sampling range.

12. The method of claim 11, wherein the sensor comprises a plurality of light sources, the method further comprising:

measuring sensor information corresponding to at least a first light source and a second light source of the plurality of light sources if the received infrared light is included in the predetermined value range; and detecting the biometric information based on the measured sensor information.

13. The method of claim 10, further comprising:

storing a plurality of measuring modes in memory, each measuring mode corresponding to at least one wavelength band; and prior to emitting the infrared light, detecting an input selecting a measuring mode from among the plurality of measuring modes, and retrieving, based on the selected measuring mode, at least one output wavelength band pre-associated with the selected measuring mode from the memory, wherein the infrared light is emitted at the selected at least one output wavelength band to acquire a desired type of the biometric information.

14. The method of claim 13, wherein the sensor comprises a light emitter and a light receiver, the light emitter including a light source emitting the infrared light, and the light receiver including a plurality of photodiodes (PDs), and wherein detecting whether the sensor is disposed parallel to the skin surface is based at least partially on symmetry of the received infrared light, as received by the plurality of photodiodes.

15. The method of claim 14, wherein when the infrared light indicates that the sensor is disposed nonparallel to the skin surface, the method further comprises applying compensation to a value received by the sensor, and detecting the biometric information using the compensated value.

16. The method of claim 10, wherein the sensor is further configured to detect, in addition to skin-related biometric information and distance, heart-related biometric information, using emission and reception of light, and wherein the sensor is configured to detect the skin-related biometric information, distance and heart-related biometric information by adjusting a wavelength of light emitted and received by the sensor.

17. The method of claim 10, further comprising emitting the infrared light by an infrared emitter included in the sensor, wherein the electronic device is interoperable with an external accessory, and at least a portion of the light emitted by the sensor is diffused and reflected by the external accessory.

18. The method of claim 17, wherein the external accessory includes a surface possessing a slope relative to the electronic device when disposed adjacent to the electronic device, and an internal cavity defining an optical path through which the infrared light travels when emitted to be detected by the sensor.

* * * * *